United States Patent
Field et al.

(10) Patent No.: US 7,131,980 B1
(45) Date of Patent: Nov. 7, 2006

(54) SURGICAL SUTURING INSTRUMENT AND METHOD OF USE

(75) Inventors: Frederic P. Field, North Hampton, NH (US); Mark Doyle, San Diego, CA (US); Albert A. LePlage, Jr., Weare, NH (US); Todd W. Frangolis, Hampton, NH (US)

(73) Assignee: DVL Acquisitions Sub, Inc., Cranston, RI (US)

( * ) Notice: Subject to any disclaimer, the term of this patent is extended or adjusted under 35 U.S.C. 154(b) by 0 days.

(21) Appl. No.: 10/051,322

(22) Filed: Jan. 18, 2002

Related U.S. Application Data

(60) Provisional application No. 60/262,588, filed on Jan. 18, 2001.

(51) Int. Cl.
*A61B 17/04* (2006.01)
*A61B 17/295* (2006.01)

(52) U.S. Cl. .................. 606/146; 606/148; 606/205

(58) Field of Classification Search ............... 606/139, 606/144, 146, 148, 145, 103
See application file for complete search history.

(56) References Cited

U.S. PATENT DOCUMENTS

| | | | |
|---|---|---|---|
| 1,449,087 A | 3/1923 | Bugbee | |
| 1,815,725 A | 7/1931 | Pilling et al. | |
| 2,579,192 A | 12/1951 | Kohl | |
| 2,613,562 A | 10/1952 | Clark | |
| 2,897,820 A | 8/1959 | Tauber | |
| 3,013,559 A | 12/1961 | Thomas | |
| 3,339,860 A * | 9/1967 | Riggles, Jr. .............. 242/602.2 | |
| 3,404,677 A | 10/1968 | Springer | |
| 3,470,875 A | 10/1969 | Johnson | |
| 3,545,444 A | 12/1970 | Green | |
| 3,584,628 A * | 6/1971 | Green ......................... 606/143 |
| 3,675,688 A | 7/1972 | Bryan et al. | |
| 3,722,309 A * | 3/1973 | Shaffer ....................... 474/169 |
| 3,735,762 A | 5/1973 | Bryan et al. | |
| 3,802,438 A | 4/1974 | Wolvek | |
| 3,807,407 A | 4/1974 | Schweizer | |
| 3,835,854 A * | 9/1974 | Jewett ........................ 604/159 |
| 3,840,017 A | 10/1974 | Violante | |
| 3,841,521 A | 10/1974 | Jarvik | |

(Continued)

FOREIGN PATENT DOCUMENTS

DE    2927143 A1    1/1980

(Continued)

OTHER PUBLICATIONS

"VCS Clip Applier System," *Auto Suture Company, A Division of United States Surgical Corporation ("USSC")*, © 1995.

*Primary Examiner*—Glenn K. Dawson
(74) *Attorney, Agent, or Firm*—Wolf Greenfield & Sacks, PC

(57) ABSTRACT

A device is disclosed for passing a flexible elongated element through a portion of a subject. In an embodiment, the device includes structure for retaining said flexible elongated element; and advancement structure for longitudinally advancing the flexible elongated element from a proximal end of the device toward a distal end of the device with sufficient force to pass the flexible elongated element through the portion of the subject. The advancement structure includes at least one drive wheel for contacting the flexible elongated element, and further wherein the at least one drive wheel contains a peripheral groove therein for receiving the flexible elongated element so as to provide increased contact area between the at least one drive wheel and the flexible elongated element.

40 Claims, 31 Drawing Sheets

U.S. PATENT DOCUMENTS

| | | | |
|---|---|---|---|
| 3,842,840 A | 10/1974 | Schweizer | |
| 3,858,783 A | 1/1975 | Kapitanov et al. | |
| 3,877,570 A | 4/1975 | Barry | |
| 3,959,960 A | 6/1976 | Santos | |
| RE28,932 E | 8/1976 | Noiles et al. | |
| 4,006,747 A | 2/1977 | Kronenthal et al. | |
| 4,027,608 A | 6/1977 | Arbuckle | |
| 4,091,880 A | 5/1978 | Troutner et al. | |
| 4,103,690 A | 8/1978 | Harris | |
| 4,109,658 A | 8/1978 | Hughes | |
| 4,161,951 A | 7/1979 | Scanlan, Jr. | |
| 4,164,225 A | 8/1979 | Johnson et al. | |
| 4,204,541 A | 5/1980 | Kapitanov | |
| 4,224,947 A | 9/1980 | Fukuda | |
| 4,235,177 A | 11/1980 | Arbuckle | |
| 4,235,238 A | 11/1980 | Ogiu et al. | |
| 4,258,716 A | 3/1981 | Sutherland | |
| 4,306,560 A | 12/1981 | Harris | |
| 4,453,661 A | 6/1984 | Genyk et al. | |
| 4,462,404 A | 7/1984 | Schwarz et al. | |
| 4,474,181 A | 10/1984 | Schenck | |
| 4,527,724 A | 7/1985 | Chow et al. | |
| 4,553,543 A | 11/1985 | Amarasinghe | |
| 4,557,265 A | 12/1985 | Andersson | |
| 4,583,541 A | 4/1986 | Barry | |
| 4,595,007 A | 6/1986 | Mericle | |
| 4,602,636 A | 7/1986 | Noiles | |
| 4,607,637 A | 8/1986 | Berggren et al. | |
| 4,610,383 A | 9/1986 | Rothfuss et al. | |
| 4,612,933 A | 9/1986 | Brinkerhoff et al. | |
| 4,624,257 A | 11/1986 | Berggren et al. | |
| 4,643,190 A | 2/1987 | Heimberger | |
| 4,644,651 A | 2/1987 | Jacobsen | |
| 4,669,473 A | 6/1987 | Richards et al. | |
| 4,705,040 A | 11/1987 | Mueller et al. | |
| 4,741,330 A | 5/1988 | Hayhurst | |
| 4,747,358 A | 5/1988 | Moll et al. | |
| 4,760,848 A | 8/1988 | Hasson | |
| 4,763,669 A | 8/1988 | Jaeger | |
| 4,803,984 A | 2/1989 | Narayanan et al. | |
| 4,819,635 A | 4/1989 | Shapiro | |
| 4,825,875 A * | 5/1989 | Ninan et al. | 600/561 |
| 4,869,414 A | 9/1989 | Green et al. | |
| 4,890,615 A * | 1/1990 | Caspari et al. | 606/146 |
| 4,898,702 A * | 2/1990 | Elkins et al. | 264/145 |
| 4,901,721 A | 2/1990 | Hakki | |
| 4,915,107 A | 4/1990 | Rebuffat et al. | |
| 4,919,152 A | 4/1990 | Ger | |
| 4,923,461 A | 5/1990 | Caspari et al. | |
| 4,935,027 A * | 6/1990 | Yoon | 606/146 |
| 4,938,214 A | 7/1990 | Specht et al. | |
| 4,941,466 A | 7/1990 | Romano | |
| 4,955,887 A | 9/1990 | Zirm | |
| 4,957,498 A | 9/1990 | Caspari et al. | |
| 4,966,600 A | 10/1990 | Songer et al. | |
| 4,997,436 A | 3/1991 | Oberlander | |
| 5,002,564 A | 3/1991 | McGregor et al. | |
| 5,004,469 A | 4/1991 | Palmieri et al. | |
| 5,021,059 A | 6/1991 | Kensey et al. | |
| 5,037,433 A | 8/1991 | Wilk et al. | |
| 5,100,042 A | 3/1992 | Gravener et al. | |
| 5,133,735 A | 7/1992 | Slater et al. | |
| 5,147,373 A | 9/1992 | Ferzli | |
| 5,161,725 A | 11/1992 | Murray et al. | |
| 5,174,300 A | 12/1992 | Bales et al. | |
| 5,181,919 A | 1/1993 | Bergman et al. | |
| 5,192,298 A | 3/1993 | Smith et al. | |
| 5,197,971 A | 3/1993 | Bonutti | |
| 5,207,697 A | 5/1993 | Carusillo et al. | |
| 5,209,747 A | 5/1993 | Knoepfler | |
| 5,211,650 A | 5/1993 | Noda | |
| 5,217,465 A | 6/1993 | Steppe | |
| 5,219,357 A | 6/1993 | Honkanen et al. | |
| 5,242,459 A | 9/1993 | Buelna | |
| 5,243,443 A | 9/1993 | Eschbach | |
| 5,254,126 A * | 10/1993 | Filipi et al. | 606/146 |
| 5,261,917 A | 11/1993 | Hasson et al. | |
| 5,290,284 A | 3/1994 | Adair | |
| 5,304,183 A | 4/1994 | Gourlay et al. | |
| 5,306,281 A | 4/1994 | Beurrier | |
| 5,308,353 A | 5/1994 | Beurrier | |
| 5,308,357 A | 5/1994 | Lichtman | |
| 5,324,308 A | 6/1994 | Pierce | |
| 5,333,625 A | 8/1994 | Klein | |
| 5,334,199 A * | 8/1994 | Yoon | 606/144 |
| 5,346,498 A * | 9/1994 | Greelis et al. | 606/108 |
| 5,356,064 A | 10/1994 | Green et al. | |
| 5,356,424 A | 10/1994 | Buzerak et al. | |
| 5,368,606 A | 11/1994 | Marlow et al. | |
| 5,370,658 A | 12/1994 | Scheller et al. | |
| 5,372,604 A | 12/1994 | Trott | |
| 5,386,741 A | 2/1995 | Rennex | |
| 5,387,221 A | 2/1995 | Bisgaard | |
| 5,389,103 A | 2/1995 | Melzer et al. | |
| 5,405,073 A | 4/1995 | Porter | |
| 5,405,344 A | 4/1995 | Williamson et al. | |
| 5,411,522 A | 5/1995 | Trott | |
| 5,417,700 A | 5/1995 | Egan | |
| 5,417,701 A | 5/1995 | Holmes | |
| 5,423,821 A | 6/1995 | Pasque | |
| 5,423,837 A | 6/1995 | Mericle et al. | |
| 5,431,670 A | 7/1995 | Holmes | |
| 5,437,681 A | 8/1995 | Meade et al. | |
| 5,447,512 A | 9/1995 | Wilson et al. | |
| 5,454,827 A | 10/1995 | Aust et al. | |
| 5,458,609 A | 10/1995 | Gordon et al. | |
| 5,465,894 A | 11/1995 | Clark et al. | |
| 5,465,895 A | 11/1995 | Knodel et al. | |
| 5,466,241 A | 11/1995 | Leroy et al. | |
| 5,474,554 A | 12/1995 | Ku | |
| 5,478,003 A | 12/1995 | Green et al. | |
| 5,478,093 A | 12/1995 | Eibl et al. | |
| 5,484,451 A | 1/1996 | Akopov et al. | |
| 5,485,947 A | 1/1996 | Olson et al. | |
| 5,489,288 A * | 2/1996 | Buelna | 606/144 |
| 5,496,334 A | 3/1996 | Klundt et al. | |
| 5,498,256 A | 3/1996 | Furnish | |
| 5,499,990 A | 3/1996 | Schulken et al. | |
| 5,500,001 A | 3/1996 | Trott | |
| 5,501,683 A | 3/1996 | Trott | |
| 5,501,688 A | 3/1996 | Whiteside et al. | |
| 5,501,692 A | 3/1996 | Riza | |
| 5,501,698 A | 3/1996 | Roth et al. | |
| 5,507,426 A | 4/1996 | Young et al. | |
| 5,520,702 A | 5/1996 | Sauer et al. | |
| 5,522,820 A | 6/1996 | Caspari et al. | |
| 5,527,321 A | 6/1996 | Hinchliffe | |
| 5,527,322 A * | 6/1996 | Klein et al. | 606/144 |
| 5,529,235 A | 6/1996 | Boiarski et al. | |
| 5,535,935 A | 7/1996 | Vidal et al. | |
| 5,545,179 A | 8/1996 | Hart | |
| 5,571,119 A | 11/1996 | Atala | |
| 5,578,044 A | 11/1996 | Gordon et al. | |
| 5,582,616 A | 12/1996 | Bolduc et al. | |
| 5,584,425 A | 12/1996 | Savage et al. | |
| 5,607,095 A | 3/1997 | Smith et al. | |
| 5,618,306 A | 4/1997 | Roth et al. | |
| 5,643,292 A * | 7/1997 | Hart | 606/144 |
| 5,643,294 A | 7/1997 | Tovey et al. | |
| 5,643,295 A | 7/1997 | Yoon | |
| 5,665,096 A | 9/1997 | Yoon | |
| 5,665,100 A | 9/1997 | Yoon | |
| 5,674,230 A | 10/1997 | Tovey et al. | |
| 5,676,674 A | 10/1997 | Bolanos et al. | |

| | | | | | | |
|---|---|---|---|---|---|---|
| 5,690,653 | A | 11/1997 | Richardson et al. | 6,454,778 B1 | 9/2002 | Kortenbach |
| 5,709,693 | A | 1/1998 | Taylor | 6,511,489 B1 | 1/2003 | Field et al. |
| 5,713,910 | A | 2/1998 | Gordon et al. | 6,514,263 B1 | 2/2003 | Stefanchik et al. |
| 5,720,766 | A | 2/1998 | Zang et al. | 6,517,553 B1 | 2/2003 | Klein et al. |
| 5,728,112 | A | 3/1998 | Yoon | 6,520,973 B1 | 2/2003 | McGarry |
| 5,735,873 | A | 4/1998 | MacLean | 6,527,785 B1 | 3/2003 | Sancoff et al. |
| 5,743,456 | A | 4/1998 | Jones et al. | 6,530,932 B1 | 3/2003 | Swayze et al. |
| 5,755,728 | A * | 5/1998 | Maki .................. 606/145 | 6,562,051 B1 | 5/2003 | Bolduc et al. |
| 5,759,188 | A | 6/1998 | Yoon | RE38,335 E | 11/2003 | Aust et al. |
| 5,762,256 | A | 6/1998 | Mastri et al. | 6,641,592 B1 | 11/2003 | Sauer et al. |
| 5,766,186 | A | 6/1998 | Faraz et al. | 6,663,641 B1 | 12/2003 | Kovac et al. |
| 5,766,217 | A | 6/1998 | Christy | 6,663,643 B1 | 12/2003 | Field et al. |
| 5,776,150 | A | 7/1998 | Nolan et al. | 6,679,895 B1 | 1/2004 | Sancoff et al. |
| 5,782,844 | A | 7/1998 | Yoon et al. | 6,682,540 B1 | 1/2004 | Sancoff et al. |
| 5,792,152 | A * | 8/1998 | Klein et al. .................. 606/144 | 6,740,099 B1 | 5/2004 | Doyle et al. |
| 5,794,834 | A | 8/1998 | Hamblin et al. | 6,755,338 B1 | 6/2004 | Hahnen et al. |
| 5,797,927 | A | 8/1998 | Yoon | 6,767,352 B1 | 7/2004 | Field et al. |
| 5,799,672 | A | 9/1998 | Hansbury | 6,786,913 B1 | 9/2004 | Sancoff et al. |
| 5,807,393 | A | 9/1998 | Williamson, IV et al. | 7,037,315 B1 * | 5/2006 | Sancoff et al. ............... 606/144 |
| 5,810,851 | A | 9/1998 | Yoon | 2002/0062136 A1 | 5/2002 | Hillstead et al. |
| 5,810,882 | A | 9/1998 | Bolduc et al. | 2002/0096550 A1 | 7/2002 | Green et al. |
| 5,814,054 | A | 9/1998 | Kortenbach et al. | 2002/0128666 A1 | 9/2002 | Sancoff et al. |
| 5,824,008 | A | 10/1998 | Bolduc et al. | 2003/0023250 A1* | 1/2003 | Watschke et al. ............ 606/148 |
| 5,830,221 | A | 11/1998 | Stein et al. | 2003/0028202 A1 | 2/2003 | Sancoff et al. |
| 5,830,234 | A | 11/1998 | Wojciechowicz et al. | 2003/0045900 A1 | 3/2003 | Hahnen et al. |
| 5,865,361 | A | 2/1999 | Milliman et al. | 2003/0105473 A1 | 6/2003 | Miller |
| 5,891,140 | A | 4/1999 | Ginn et al. | 2003/0105475 A1 | 6/2003 | Sancoff et al. |
| 5,893,863 | A | 4/1999 | Yoon | 2003/0105476 A1 | 6/2003 | Sancoff et al. |
| 5,895,395 | A | 4/1999 | Yeung | 2003/0114863 A1 | 6/2003 | Field et al. |
| 5,897,562 | A | 4/1999 | Bolanos et al. | 2003/0135226 A1 | 7/2003 | Bolduc et al. |
| 5,911,727 | A | 6/1999 | Taylor | 2003/0171761 A1 | 9/2003 | Sancoff et al. |
| 5,919,202 | A | 7/1999 | Yoon | 2004/0073237 A1 | 4/2004 | Leinsing |
| 5,922,001 | A | 7/1999 | Yoon | 2004/0087979 A1 | 5/2004 | Field et al. |
| 5,922,002 | A | 7/1999 | Yoon | 2004/0092967 A1 | 5/2004 | Sancoff et al. |
| 5,951,575 | A | 9/1999 | Bolduc et al. | 2004/0108357 A1 | 6/2004 | Milliman et al. |
| 5,954,731 | A | 9/1999 | Yoon | 2004/0133221 A1 | 7/2004 | Sancoff et al. |
| 5,972,004 | A | 10/1999 | Williamson, IV et al. | 2004/0158267 A1 | 8/2004 | Sancoff et al. |
| 5,984,938 | A | 11/1999 | Yoon | 2004/0254592 A1 | 12/2004 | DiCarlo et al. |
| 6,030,410 | A | 2/2000 | Zurbrugg | 2005/0038449 A1 | 2/2005 | Sancoff et al. |
| 6,032,849 | A | 3/2000 | Mastri et al. | 2005/0043747 A1 | 2/2005 | Field et al. |
| 6,048,351 | A | 4/2000 | Gordon et al. | 2005/0070922 A1 | 3/2005 | Field et al. |
| 6,074,404 | A | 6/2000 | Stalker et al. | | | |
| 6,099,537 | A | 8/2000 | Sugai et al. | | | |

FOREIGN PATENT DOCUMENTS

| | | | |
|---|---|---|---|
| 6,109,500 | A | 8/2000 | Alli et al. |
| 6,119,913 | A | 9/2000 | Adams et al. | 
| 6,131,790 | A | 10/2000 | Piraka |

| | | |
|---|---|---|
| EP | 121362 A1 | 10/1984 |
| EP | 216532 A1 | 4/1987 |
| EP | 646356 A2 | 4/1995 |
| EP | 705569 A1 | 4/1996 |
| EP | 741996 A2 | 11/1996 |
| GB | 2025236 A | 1/1980 |
| WO | WO 93/16644 A1 | 9/1993 |
| WO | WO 95/18572 A1 | 7/1995 |
| WO | WO 96/10957 A1 | 4/1996 |
| WO | WO 96/27331 A1 | 9/1996 |
| WO | WO 98/11829 A1 | 3/1998 |
| WO | WO 02/34167 A2 | 5/2002 |
| WO | WO 02/43569 A2 | 6/2002 |
| WO | WO 03/101313 A1 | 12/2003 |

| | | | |
|---|---|---|---|
| 6,139,520 | A * | 10/2000 | McCrory et al. .............. 604/60 |
| 6,171,316 | B1 | 1/2001 | Kovac et al. |
| 6,187,019 | B1* | 2/2001 | Stefanchik et al. ......... 606/144 |
| 6,206,893 | B1 | 3/2001 | Klein et al. |
| 6,241,139 | B1 | 6/2001 | Milliman et al. |
| 6,273,860 | B1 | 8/2001 | Kostylev et al. |
| 6,296,656 | B1 | 10/2001 | Bolduc et al. |
| 6,302,311 | B1 | 10/2001 | Adams et al. |
| 6,330,965 | B1 | 12/2001 | Milliman et al. |
| 6,331,182 | B1 | 12/2001 | Tiefenbrun et al. |
| 6,332,889 | B1 | 12/2001 | Sancoff et al. |
| 6,383,208 | B1 | 5/2002 | Sancoff et al. |
| 6,439,446 | B1 | 8/2002 | Perry et al. |
| 6,443,973 | B1 | 9/2002 | Whitman |

* cited by examiner

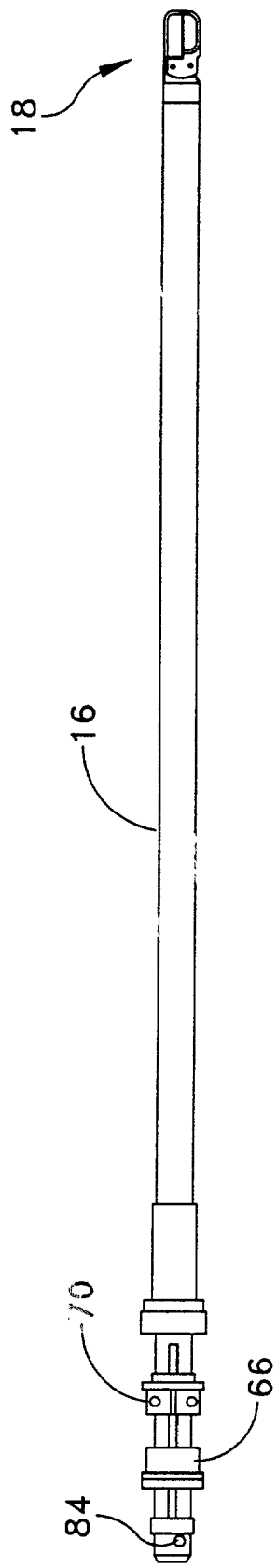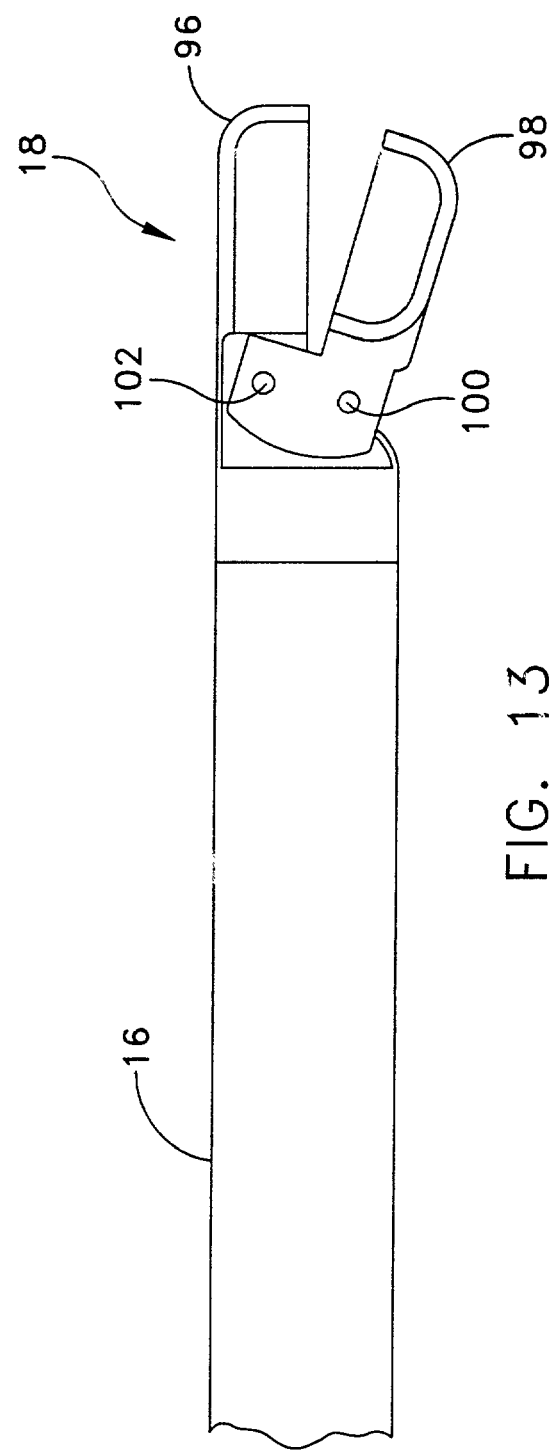
FIG. 12
FIG. 13

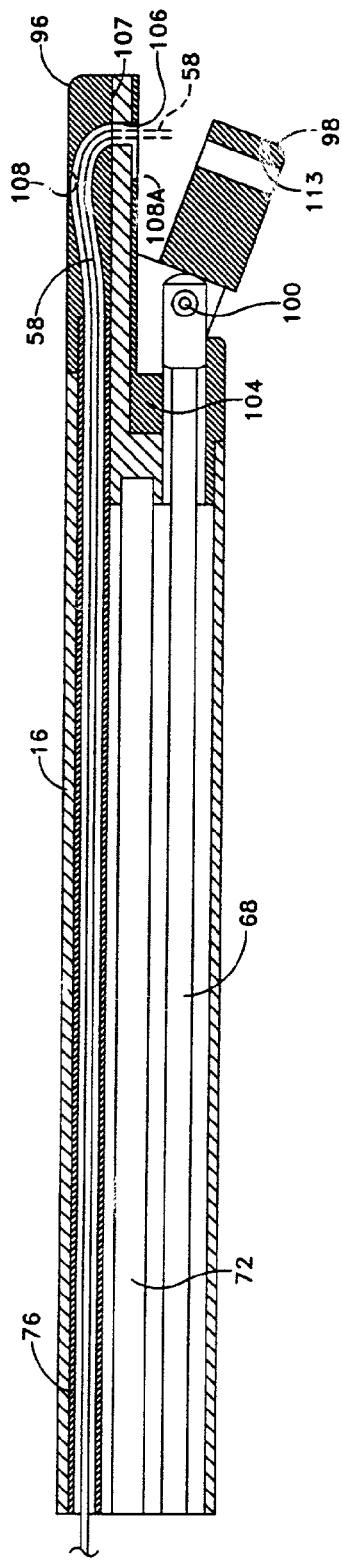

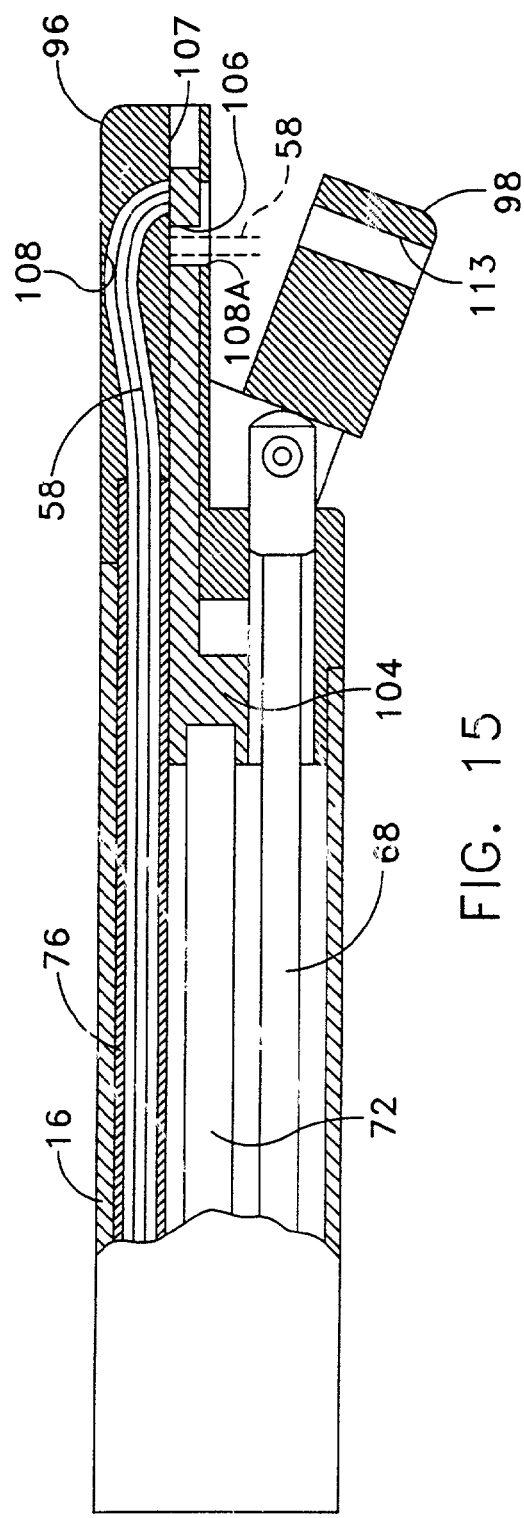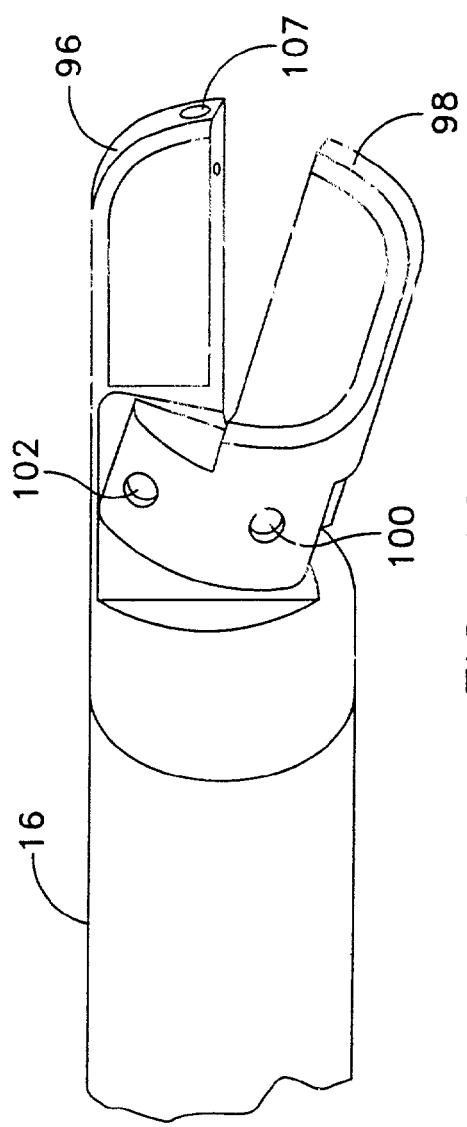

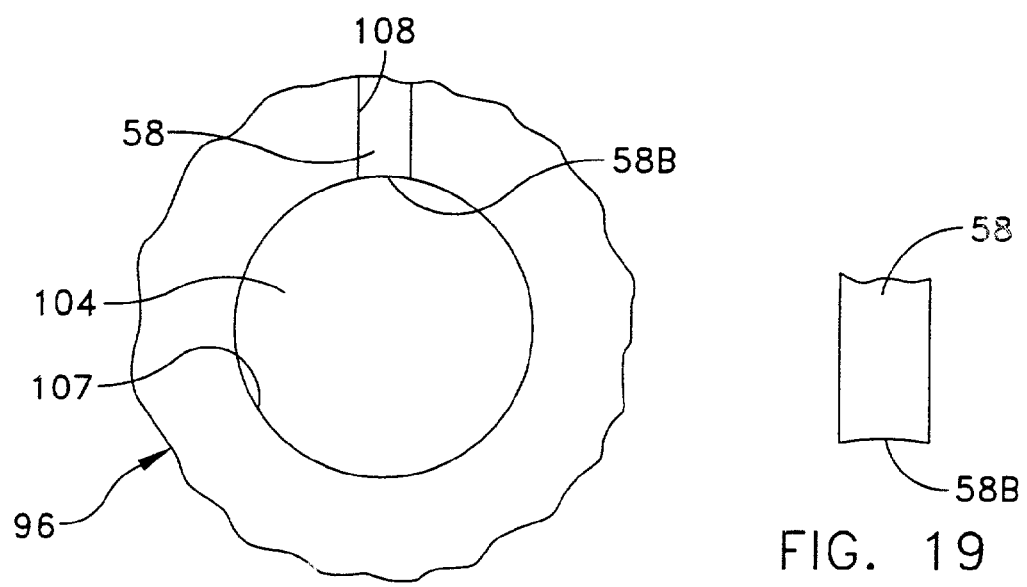
FIG. 18
FIG. 19
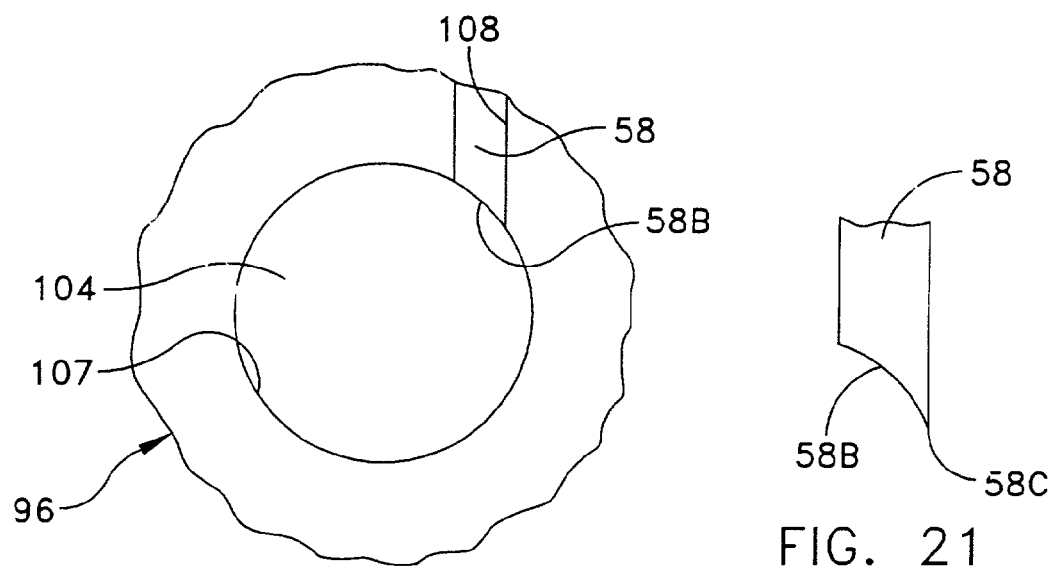
FIG. 20
FIG. 21

SURGICAL SUTURING INSTRUMENT AND METHOD OF USE

REFERENCE TO EARLIER APPLICATIONS

The present application claims the benefit of prior U.S. Provisional Patent Application Ser. No. 60/262,588, filed Jan. 18, 2001, now abandoned, by Frederic P. Field et al. for SURGICAL SUTURING INSTRUMENT AND METHOD OF USE, which is hereby incorporated herein by reference.

FIELD OF THE INVENTION

This invention relates to medical suturing instruments, and more particularly to drive means in such instruments for advancing a suture strand toward a suturing site.

BACKGROUND OF THE INVENTION

Suturing instruments are typically used to draw together two or more portions of a subject patient (e.g., tissue such as muscle or skin) or to attach an object to the patient (e.g., to attach a piece of surgical mesh to the abdominal wall of the patient during hernia repair surgery).

Certain suturing instruments employ a needle that precedes a length of suture material through a subject.

For example, U.S. Pat. Nos. 3,470,875; 4,027,608; 4,747,358; 5,308,353; 5,674,230; 5,690,653; 5,759,188; and 5,766,186 generally disclose suturing instruments in which a needle, with trailing suture material, is passed through a subject.

U.S. Pat. Nos. 4,890,615; 4,935,027; 5,417,700; and 5,728,112 generally disclose suturing instruments in which suture material is passed through the end of a hollow needle after that needle has passed through a subject.

With all of the foregoing devices, a needle must be passed through the subject in order to deploy the suture. This is generally undesirable, since the needle typically leaves a larger hole in the subject than is necessary to accommodate only the suture material. In this respect it should be appreciated that it is generally desirable to alter each portion of the material being sutured as little as possible.

A suturing instrument has been devised which permits the suture material itself to pierce the subject without the use of a needle. However, this device does not permit sufficient flexibility with regard to the amount of tension that may be applied to the suture and tissue.

More particularly, U.S. Pat. No. 5,499,990 discloses a suturing instrument in which a 0.25 mm stainless steel suturing wire is advanced to the distal end of a suturing instrument, whereupon the distal end of the suturing wire is caused to travel in a spiral direction so as to effect stitches joining together two portions of a subject. After the spiral is formed, the beginning and end portions of the suture may be bent toward the tissue in order to inhibit retraction of the suture wire into the tissue upon removal of the suturing instrument. The stainless steel wire is sufficiently firm to hold this locking set. In addition, after the spiral is formed, the radius of the deployed suture spiral may then be decreased by advancing an outer tube over a portion of the distal end of the instrument. Again, the stainless steel wire is sufficiently firm to hold this reducing set.

Unfortunately, however, such a system does not permit sufficient flexibility in all situations with regard to the appropriate amount of tension to be applied to the subject, since the wire is relatively firm (i.e., firm enough to hold its sets). Such a system also does not provide sufficient flexibility with regard to the appropriate type of suture stitch to be applied, since the device is specifically configured to provide only a spiral suture stitch.

In contrast to the aforementioned limitations of the suturing instrument of U.S. Pat. No. 5,499,990, it is desirable that a suturing instrument approximate the portions of the material which is to be joined in the correct physiological relationship, and to urge the portions together with an appropriate amount of force. If too much force (or tension) is applied to the suture material, then the subject portions may become necrotic or the sutures may cut through the subject. If too little tension is applied to the suture material, then the healing process may be impaired.

U.S. Pat. No. 4,453,661 discloses a surgical instrument for applying staples. The staples are formed from the distal end of a length of wire. The distal end of the wire is passed through a subject, and thereafter contacts a die that causes the wire to bend, thereby forming the staple. The wire is sufficiently firm to take the set imposed by the die. The staple portion is then cut from the wire by a knife. Again, such a system suffers from the fact that it does not permit sufficient flexibility in all situations with regard to the appropriate tension to be applied to the subject, since the attachment is made by a staple which has a predefined geometry and is formed with relatively firm wire. In addition, the system is limited as to the type of fastening which may be applied, since the surgical instrument is limited to only applying wire staples.

There is a need, therefore, for a new suturing device that permits minimally disruptive suturing and permits flexibility in the placement, application, and tensioning of the suture material.

SUMMARY OF THE INVENTION

The invention provides a device for introducing a flexible elongated element through a subject. In one embodiment, the device includes a proximal end and a distal end, as well as an advancement unit for longitudinally advancing the flexible elongated element toward the distal end of the device such that a distal end of the flexible elongated element may pass from the distal end of the device with sufficient force to pass through the subject. The device also includes a securing unit for variably adjusting a securing force applied by the flexible elongated element so as to provide the desired securement to the subject.

In further embodiments, the device includes a guide tube for guiding the flexible elongated element through the device, toward the distal end of the device, as well as a rotation unit for rotating the distal end of the device so as to cause the flexible elongated element to wrap around itself, whereby to adjustably apply the securing force to the flexible elongated element.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein:

FIG. 12 is a side view of a shaft and an end effector portion of the suturing instrument shown in FIG. 1;

FIG. 13 is a side view of the end effector portion of the suturing instrument shown in FIG. 1;

FIG. 14 is a side view, partially in section, of the end effector portion shown in FIG. 13, with the end effector portion being shown with its cutting bar in its forward (i.e., non-cutting) position;

FIG. 15 is a side view, partially in section, of the end effector portion shown in FIG. 14, but with the end effector portion being shown with its cutting bar in its retracted (i.e., cutting) position;

FIG. 16 is a perspective view of the end effector portion of the suturing instrument shown in FIG. 1;

FIG. 18 is a sectional view showing one possible construction for the suturing instrument's fixed jaw portion and its associated cutting bar;

FIG. 19 is a side view showing a piece of wire cut with the apparatus shown in FIG. 18;

FIG. 20 is a sectional view showing another possible fixed construction for the suturing instrument's fixed jaw portion and its associated cutting bar;

FIG. 21 is a side view showing a piece of wire cut with the apparatus shown in FIG. 20;

DETAILED DESCRIPTION OF THE PREFERRED EMBODIMENT

Overview

Figure 1:
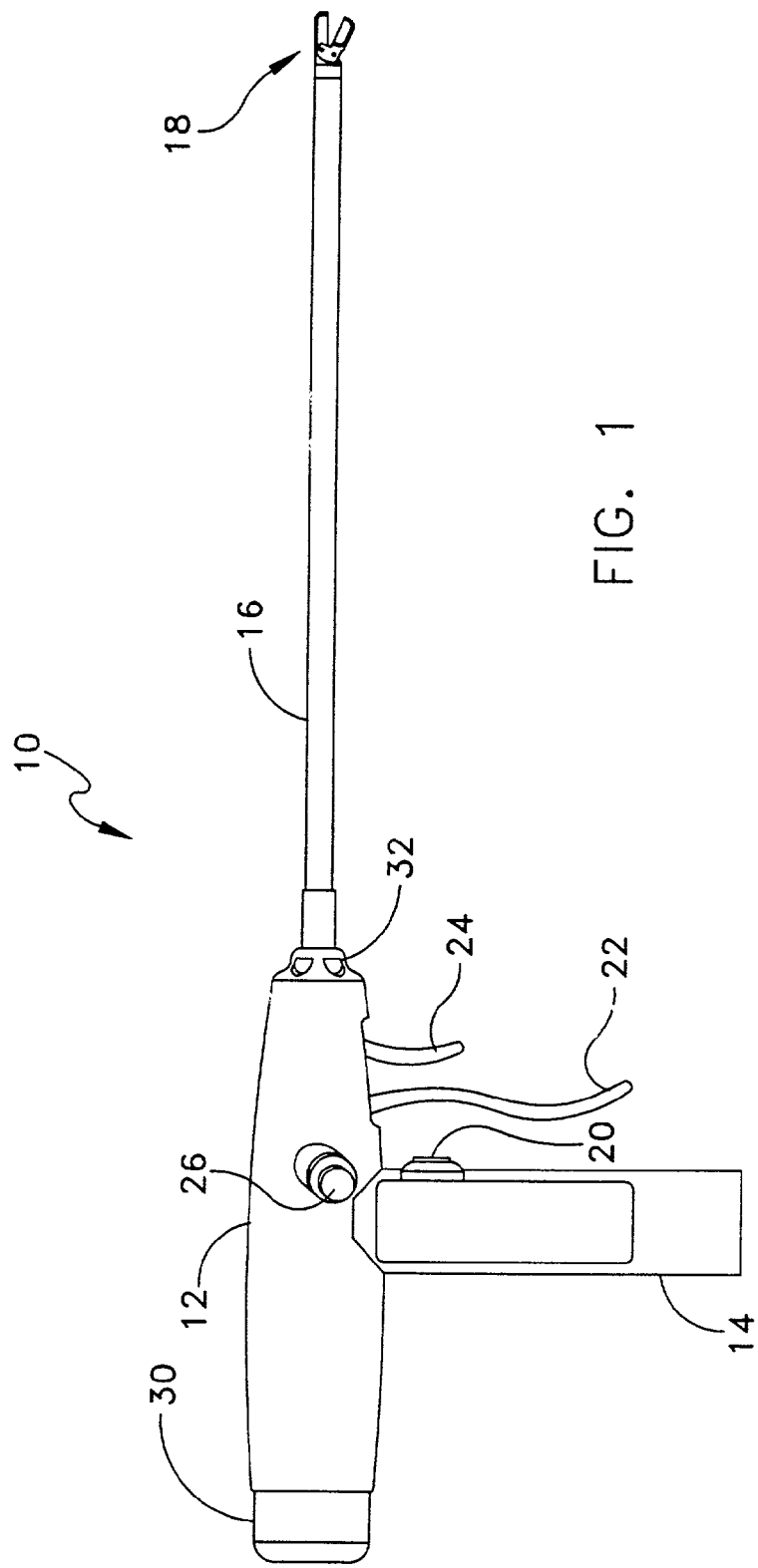
FIG. 1 is a side view of a suturing instrument formed in accordance with the present invention.
Figure 3:
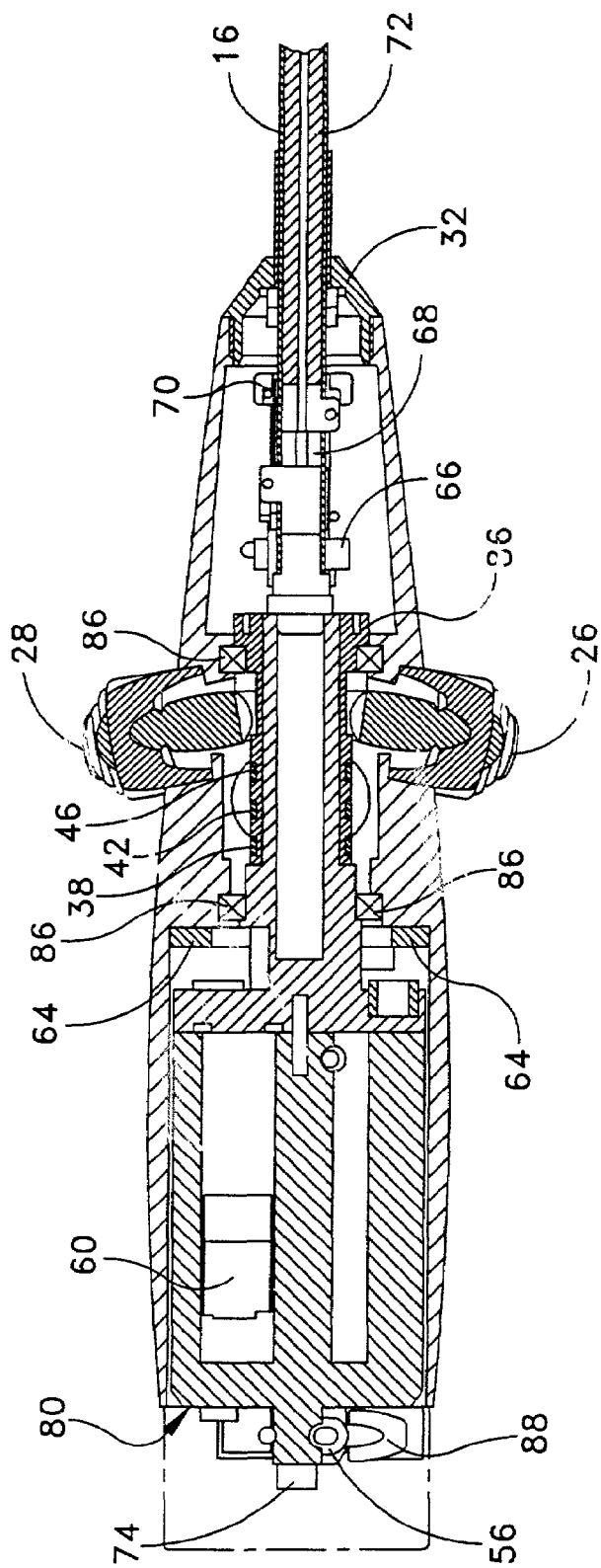
FIG. 3 is a partial top view, partially in section, of the suturing instrument shown in FIG. 1.

Looking first at FIG. 1, there is shown a suturing instrument 10 which comprises a preferred embodiment of the present invention. Suturing instrument 10 includes a housing 12, a handle 14, a shaft 16 and an end effector 18. Suturing instrument 10 also includes a wire advance button 20, a jaw closing actuator 22, a wire cutting actuator 24, a left-thumbactuated rotation button 26, and a right-thumb-actuated rotation button 28 (FIG. 3). Suturing instrument 10 also includes a wire supply cartridge 30, as well as a shaft retaining nut 32. Shaft retaining nut 32 allows shaft 16 to be dismounted from the remainder of the device for cleaning purposes.

As will be discussed in further detail below, generally during use, suture wire (comprising wire formed of metal or any other suitable material having the required flexibility and stiffness) is drawn from a winding in wire supply cartridge 30 and is pushed through housing 12 and shaft 16 to end effector 18, which includes a pair of opposing jaw portions. The jaw portions may be brought together around the material which is to be sutured by actuating jaw closing actuator 22 when the jaw portions are positioned at an appropriate surgical location. The suture wire is driven through housing 12 and shaft 16 to end effector 18 by actuating wire advance button 20. The suture wire is driven from one jaw portion to the other jaw portion with sufficient force to penetrate the tissue placed between the jaw portions, and the suture wire is permitted to pass through the second jaw portion. The jaw portions are then permitted to separate and move away from the tissue, leaving the suture wire extending from the subject tissue to each of the two jaw portions. Shaft 16 and end effector 18 (together with wire supply cartridge 30) may then be rotated with respect to housing 12 and handle 14 by actuating either left-thumb-actuated rotation button 26 or right-thumb-actuated rotation button 28. This causes the portions of the suture wire that extend from the tissue to be twisted about one another so as to form a closed loop extending through the tissue. It will be appreciated that the size of this closed loop may be adjustably reduced by increasing the degree of twisting in the wire. The twisted loop of suture wire may then be cut off, at end effector 18, from the remaining portion of the suture wire that extends back through the suturing instrument. Such cutting may be effected by actuating wire cutting actuator 24.

As will be discussed in further detail below, wire supply cartridge 30 may be supplied separately from suturing instrument 10, with the wire supply cartridge 30 being loaded into suturing instrument 10 prior to commencing a suturing operation. As will also be discussed in further detail below, wire supply cartridge 30 may be disposable, such that the cartridge may be discarded after all of its wire has been used up.

Construction Details

Figure 2:
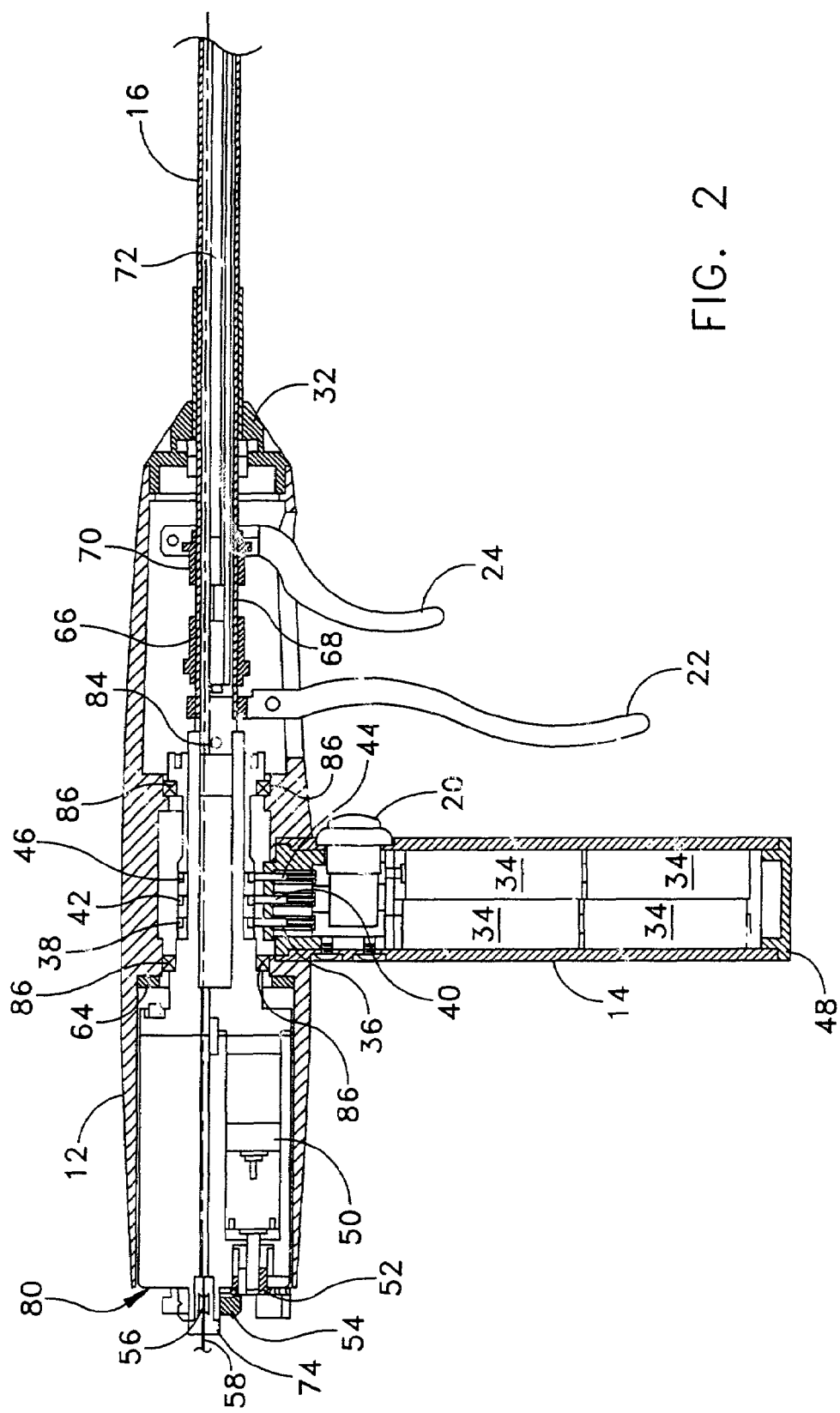
FIG. 2 is a partial side view, partially in section, of the suturing instrument shown in FIG. 1.
Figure 4:
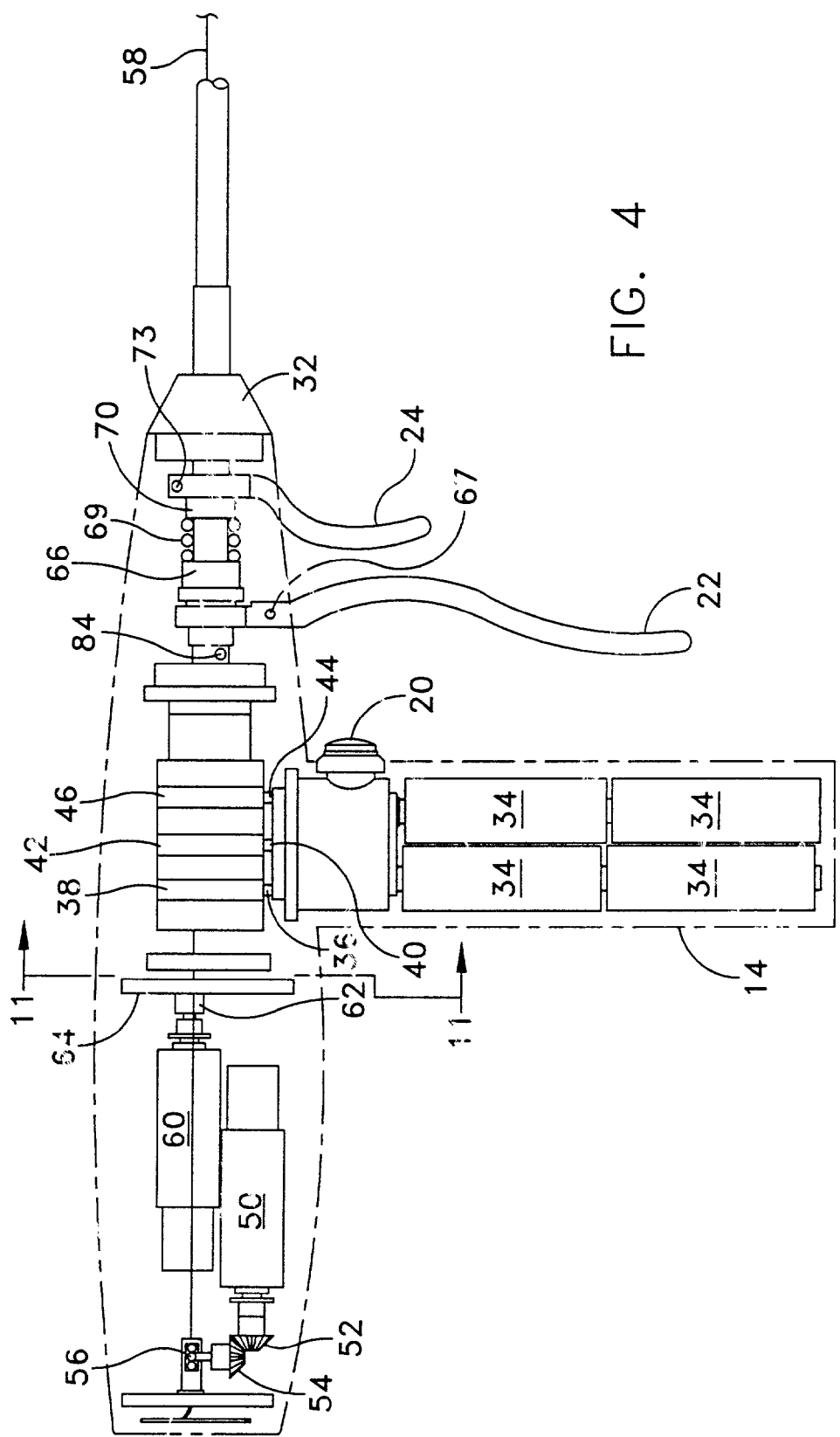
FIG. 4 is a schematic partial side view showing some of the internal components of the suturing instrument shown in FIG. 1.

As shown in FIGS. 2 and 4, handle 14 provides a cavity that may receive batteries 34. In other embodiments, the unit may be powered remotely via a power transmission cord or any other source of suitable power.

Batteries 34 supply a ground (or negative) potential to a ground connector post 36 (FIG. 2), which in turn communicates with a rotary ground communicator 38. Rotary ground communicator 38 permits electrical contact to be maintained with ground connector post 36 when rotary ground communicator 38 is rotated with respect to ground connector post 36, as occurs when shaft 16 and end effector 18 are rotated so as to twist closed suture wire extending through the tissue.

Batteries 34 supply a positive potential to wire advance button 20, and to a first connector post 40, which in turn communicates with a first rotary electrical communicator 42. First rotary electrical communicator 42 permits electrical contact to be maintained with first connector post 40 when first rotary electrical communicator 42 is rotated with respect to first connector post 40. The positive potential from batteries 34 is also supplied (in parallel) to each thumb-activated rotation button 26, 28 (FIG. 3), and to a second connector post 44 (FIG. 2), which in turn communicates with a second rotary electrical communicator 46. Again, second rotary electrical communicator 46 permits electrical contact to be maintained with second connector post 44 when second rotary electrical communicator 46 is rotated with respect to second connector post 44. Each of the connector posts 36, 40 and 44 may be spring-biased so as to remain in contact with its respective rotary communicator. In view of the foregoing construction, the positive potentials may be switched on by depressing the respective actuator button 20, 26, 28. Handle 14 also includes a cap 48 which may be removed so as to permit insertion of batteries 34.

First rotary electrical communicator 42 is in electrical communication with a wire advance motor 50 shown in FIGS. 2 and 4. The output shaft of wire advance motor 50 is coupled to a miter drive gear 52, which is in turn coupled to a miter follower gear 54. Miter follower gear 54 is coupled to a drive wheel 56 which contacts a suture wire 58, as will be described in further detail below with reference to FIGS. 5–10.

Figure 4A:
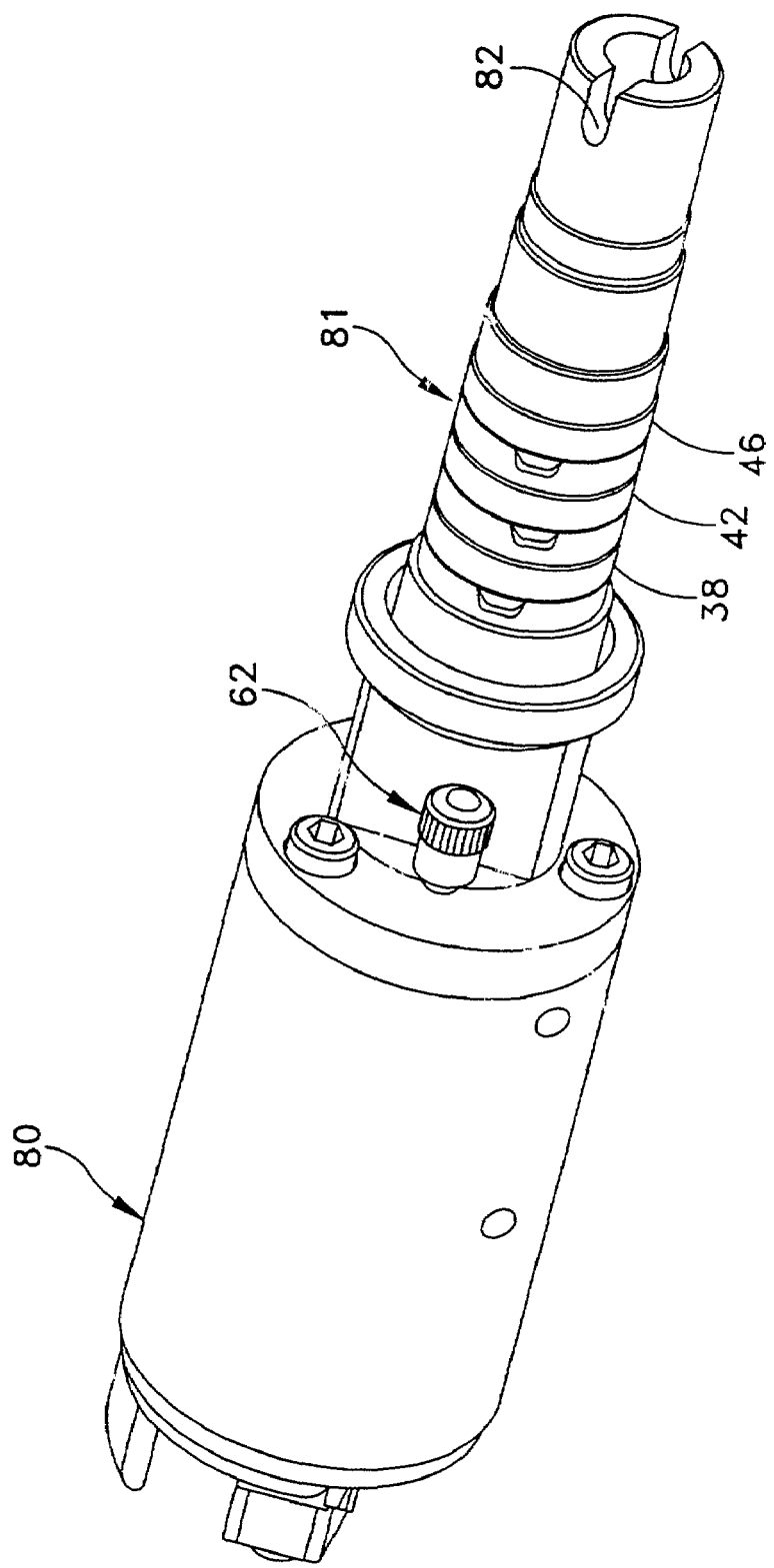
FIG. 4A is a perspective view of a drive barrel assembly incorporated in the suturing instrument shown in FIG. 1.
Figure 11:
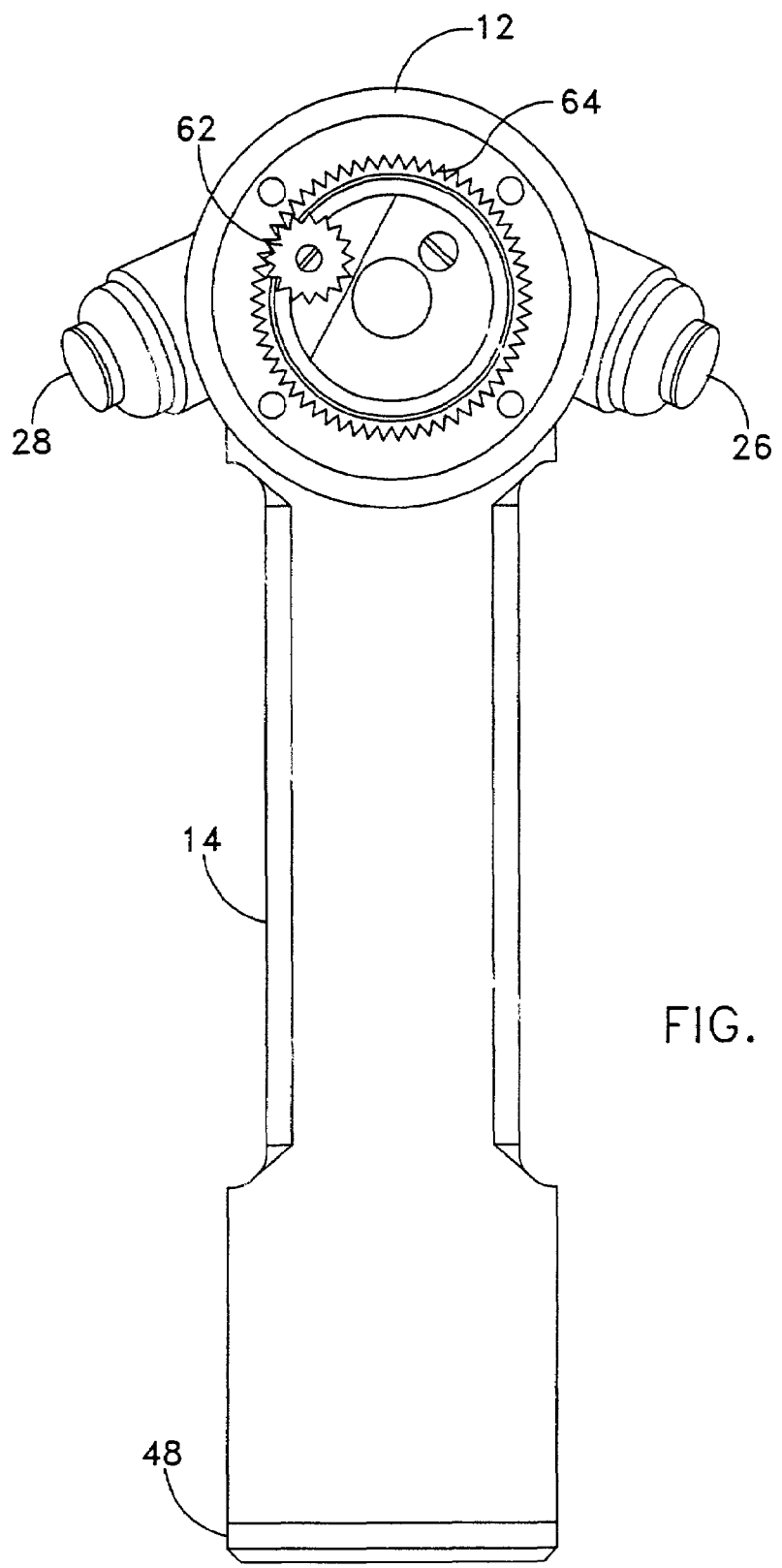
FIG. 11 is a schematic view taken along the line 11—11 of FIG. 4.

Second rotary electrical communicator 46 is in electrical communication with a shaft rotation motor 60 (FIGS. 3 and 4), the output of which is coupled to a pinion gear 62 (FIGS. 4, 4A and 11) that rotates along an internal gear 64 (FIGS. 4 and 11). As shown in FIG. 3, left-thumb-actuated rotation button 26 and right-thumb-activated rotation button 28 may be provided to permit the user to use the thumb of either their left hand or their right hand, respectively, so as to actuate shaft rotation motor 60. In this respect it will be appreciated that, inasmuch as left-thumb-actuated rotation button 26 and right-thumb-actuated rotation button 28 are wired in parallel, shaft rotation motor 60 will rotate in the same direction regardless of which button (i.e., button 26 or button 28) may be actuated.

Jaw closing actuator 22 (FIGS. 2 and 4) is coupled to a jaw linkage coupler 66, which in turn contacts a jaw linkage 68 (FIGS. 2 and 14). When jaw closing actuator 22 is pulled toward handle 14 (FIG. 2), jaw closing actuator 22 pivots on its pivot pin 67 (FIG. 4) so as to drive jaw linkage coupler 66 distally, against the force of biasing spring 69, and so as to cause the jaw linkage 68 to move forward toward the distal end of suturing instrument 10. This action will in turn cause a movable jaw portion 98 to close on a fixed jaw portion 96 (FIG. 17A), as will hereinafter be discussed in further detail. When jaw closing actuator 22 is subsequently released, biasing spring 69 (FIG. 4) drives jaw linkage coupler 66 proximally, so as to cause jaw linkage 68 to move proximally. This action will cause movable jaw portion 98 to open relative to fixed jaw portion 96 (FIG. 14), as will hereinafter be discussed in further detail. The action of jaw linkage 68 at the distal end of the device is discussed further below with reference to FIGS. 13 and 14.

Wire cutting actuator 24 is coupled to a wire cutting linkage coupler 70 (FIGS. 2 and 4), which in turn contacts a wire cutting linkage 72 (FIGS. 2, 14 and 15). When wire cutting actuator 24 is pulled toward handle 14 (FIG. 2), wire cutting actuator 24 pivots on its pivot pin 73 (FIG. 4) so as to drive wire cutting linkage coupler 70 proximally, against the force of biasing spring 69, and so as to cause wire cutting linkage 72 to move proximally, away from the distal end of suturing instrument 10. This action will in turn cause a cutting bar 104 (FIG. 14) to move proximally (FIG. 15) so as to effect wire cutting, as will hereinafter be discussed in further detail. When wire cutting actuator 24 is subsequently released, biasing spring 69 drives wire cutting linkage coupler 70 distally, so as to cause wire cutting linkage 72 to move distally. This action causes the cutting bar 104 to move distally, so as to assume the position shown in FIG. 14. Wire cutting linkage 72 moves adjacent to, and independent of, jaw linkage 68 discussed above. The action of wire cutting linkage 72 at the distal end of the device is discussed further below with reference to FIGS. 14 and 15.

Figure 5:
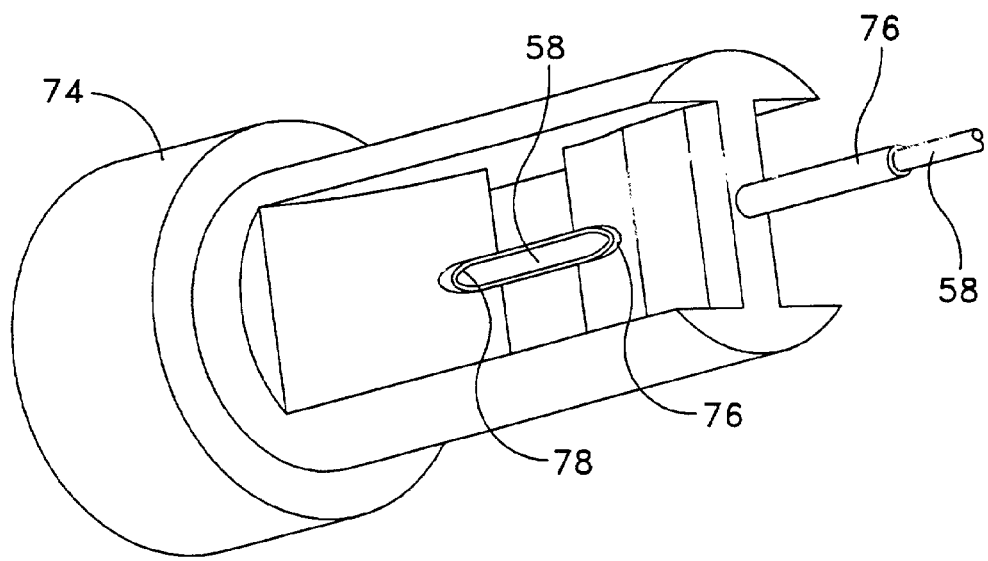
FIG. 5 is a perspective view of a wire guide support unit incorporated in the suturing instrument shown in FIG. 1.
Figure 6:
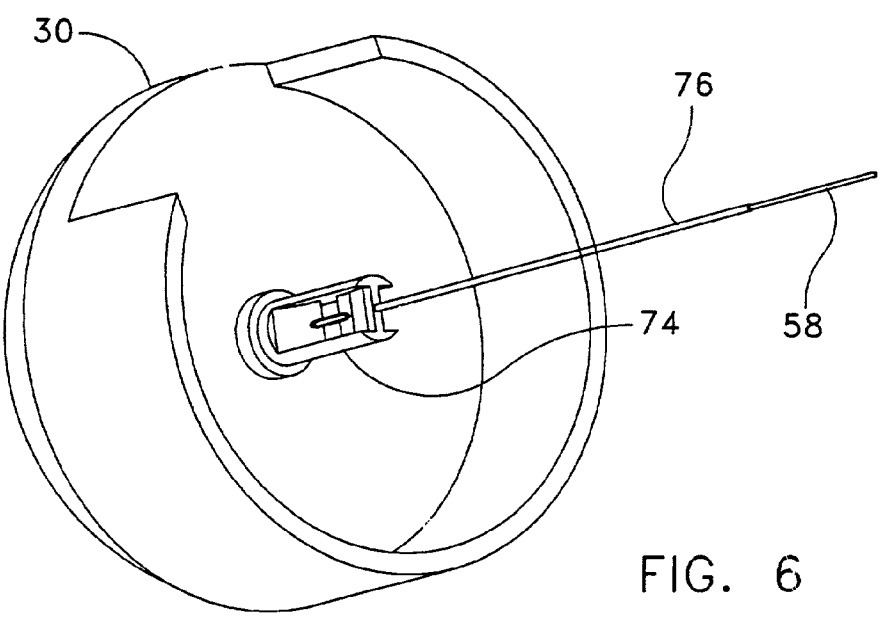
FIG. 6 is a perspective view of the suturing instrument's wire supply cartridge, which includes the wire guide support unit shown in FIG. 5.
Figure 7:
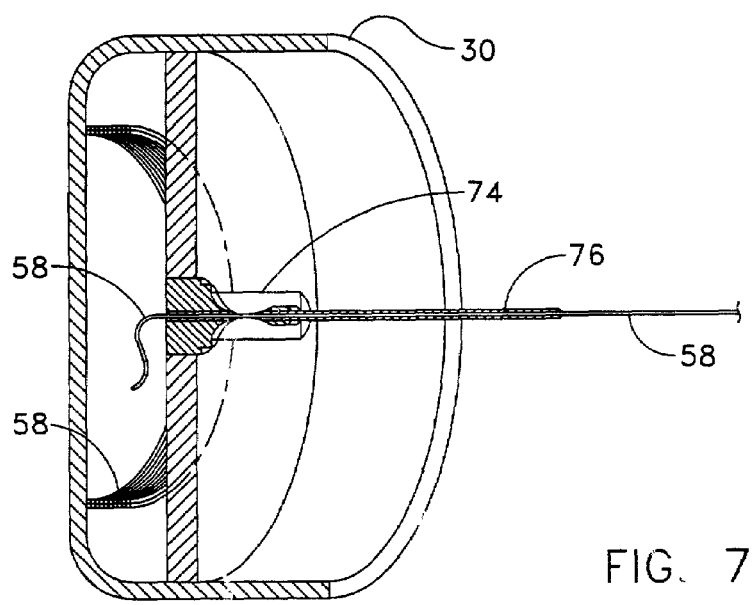
FIG. 7 is a perspective view, partially in section, of the wire supply cartridge shown in FIG. 6.
Figure 8:
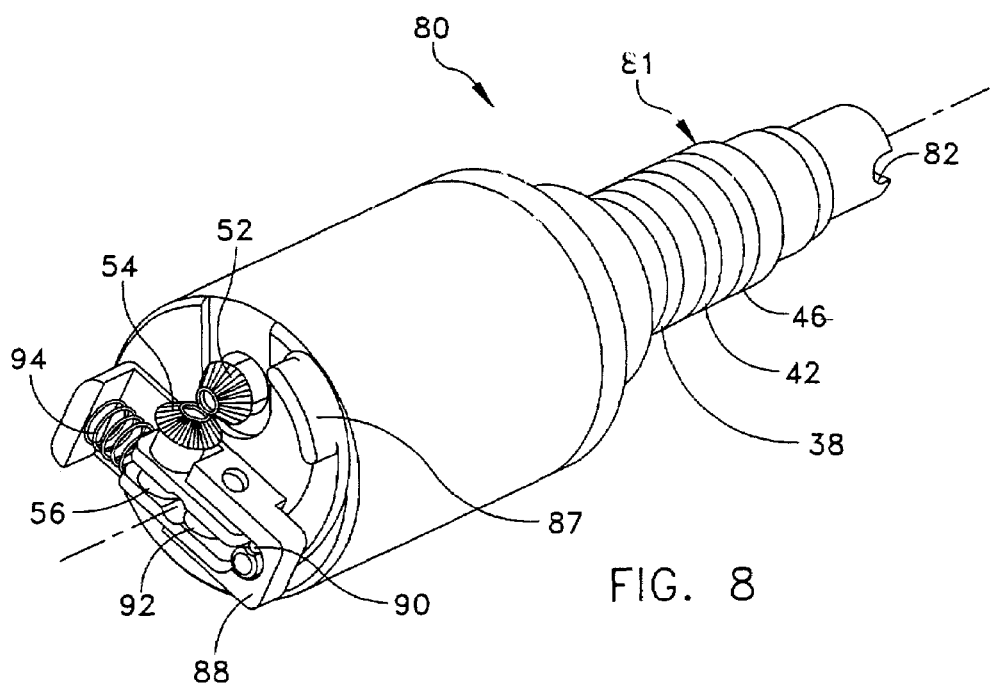
FIG. 8 is a perspective rear view of the drive barrel assembly incorporated in the suturing instrument shown in FIG. 1, with the drive barrel assembly's release lever being shown in its closed position.
Figure 9:
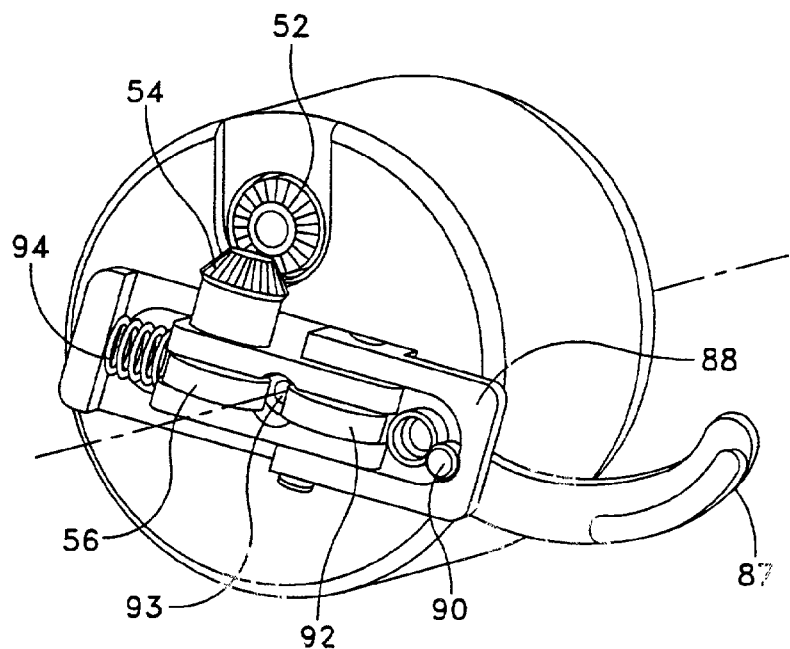
FIG. 9 is a perspective view of the proximal (i.e., rear) end of the drive barrel assembly shown in FIG. 8, with the release lever being shown in its open position.
Figure 10:
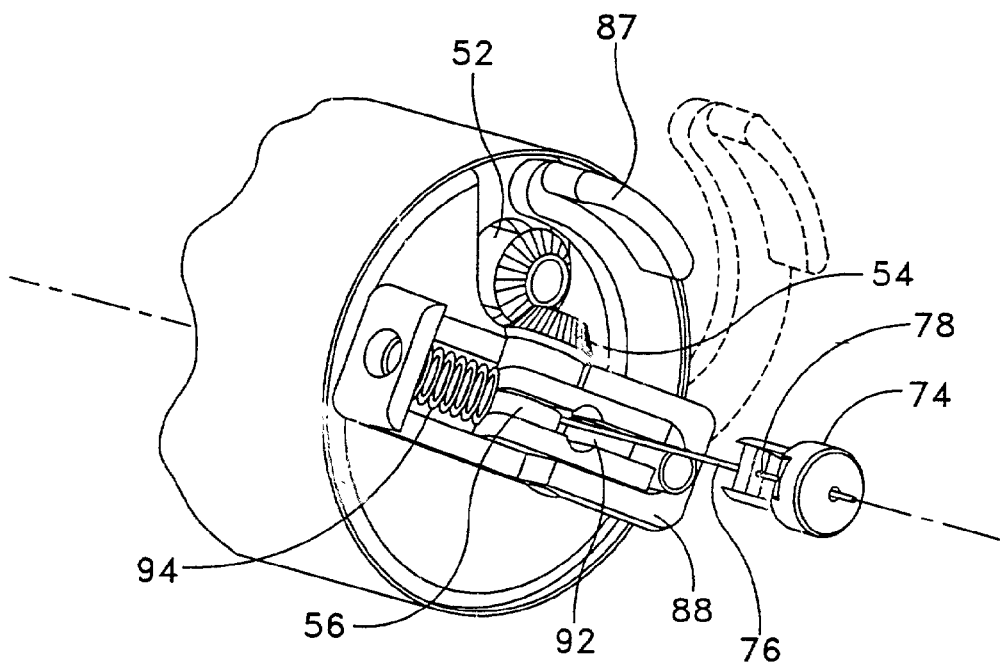
FIG. 10 is a perspective view of the proximal (i.e., rear) end of the same drive barrel assembly, with the release lever being shown in its closed position, and with the wire guide and wire guide support unit being advanced relative to the drive barrel assembly (but with the remainder of the wire supply cartridge being removed from view)

The wire supply cartridge 30 shown in FIG. 1 includes a wire guide support unit 74, as shown in FIGS. 5–7. A supply coil of suture wire 58 (comprising wire formed of metal or any other suitable material having the required flexibility and stiffness) may be supplied in the base of cartridge 30 and is fed into the support unit 74 as shown in FIG. 7. A wire guide 76 surrounds suture wire 58, from support unit 74 to the distal end of suturing instrument 10, adjacent to end effector 18 (FIGS. 5–7, 14 and 15). Wire guide 76 ensures that suture wire 58 does not bend or buckle as the suture wire is pushed through housing 12 and shaft 16. More particularly, wire guide 76 preferably forms a sufficiently close sliding fit with suture wire 58 such that suture wire 58 cannot bend or buckle as the suture wire is advanced through suturing instrument 10. At the same time, wire guide 76 is also formed so as to present a minimum of friction to suture wire 58 as the suture wire is advanced through the instrument. The foregoing characteristics are important, inasmuch as suture wire 58 is extremely thin and flexible and highly susceptible to bending or buckling in the absence of some sort of lateral support.

By way of example but not limitation, where suture wire 58 is formed out of stainless steel and has a diameter of 0.005 inch, wire guide 76 might have an inside diameter of 0.008 inch and an outside diameter of 0.016 inch. In addition, wire guide 76 is preferably formed out of polytetrafluoroethylene (PTFE) or some other relatively lubricious material. Alternatively, the interior of wire guide 76 may be coated with a lubricant so as to facilitate closely-supported, low-friction passage of the suture wire through the wire guide.

Further by way of example but not limitation, in one preferred form of the invention, suture wire 58 may comprise 316 LVM stainless steel having a tensile strength of 170 kpsi.

Although wire guide 76 extends through support unit 74 (FIG. 7), wire guide 76 has two openings 78 (one on either side of wire guide 76, only one of which is shown in FIG. 5) in the center of support unit 74. Openings 78 expose a portion of suture wire 58 so that wire drive wheel 56 (FIG. 8) may contact suture wire 58 and urge the suture wire forward toward the distal end of suturing instrument 10, as will be discussed in detail below with reference to FIGS. 8–10.

As shown in FIGS. 2, 3, 4A and 8, housing 12 receives a drive barrel assembly 80 that contains the aforementioned motors 50 and 60, and provides a distally-extending barrel shaft 81 (FIGS. 4A and 8), on the outside of which are located the rotary communicators 38, 42 and 46. A recess 82 (FIG. 4A) is provided on the distal end of barrel shaft 81 for receiving a coupling pin 84 (FIGS. 2 and 4) which is located on the proximal end of shaft 16, such that rotation of drive barrel assembly 80 causes rotation of coupling pin 84 and hence shaft 16. Drive barrel assembly 80 is rotationally held within housing 12 by bearings 86, as shown in FIGS. 2 and 3.

Looking next at FIGS. 7–10, wire supply cartridge 30 may be attached to drive barrel assembly 80 by rotating a release lever 87 away from the center of drive barrel assembly 80 (FIGS. 8 and 9), so as to move a carriage 88 relative to drive barrel assembly 80. Most particularly, release lever 87 rides on a pin 90, and rotation of release lever 87 from the position shown in FIG. 8 to the position shown in FIG. 9 draws carriage 88, as well as a wire follower wheel 92, away from the center of drive barrel assembly 80. Once wire follower wheel 92 is separated from wire drive wheel 56 by a sufficient distance to expose the drive barrel assembly's central passageway 93 (FIG. 9), wire guide 76 (overlying suture wire 58) may be inserted into passageway 93 (FIG. 10), and wire guide support unit 74 (FIGS. 6, 7 and 10) may be inserted between wheels 56 and 92 (FIG. 10), such that wheels 56 and 92 contact either side of suture wire 58 through openings 78 formed in either side of wire guide 76. A biasing spring 94 (FIGS. 8–10) is provided on carriage 88 to urge wire follower wheel 92 into close contact with suture wire 58. In other embodiments, wire follower wheel 92 may also be driven indirectly by wire drive wheel 56 in order to provide additional forces to move suture wire 58 distally (i.e., forward, toward the tool's end effector 18).

Pinion gear 62 (FIGS. 4, 4A and 11) extends distally from drive barrel assembly 80 and engages the housing's internal gear 64, as shown in FIGS. 4 and 11. As a result of this construction, when shaft rotation motor 60 is actuated, pinion gear 62 rotates around internal gear 64, bringing with it the entire drive barrel assembly 80. This in turn causes shaft 16 to rotate, since shaft 16 is coupled to drive barrel assembly 80. More particularly, the rotation of drive barrel assembly 80 is transferred to shaft 16 through the shaft's coupling pin 84 (FIGS. 2, 4 and 12), which is seated in recess 82 (FIG. 8) of drive barrel assembly 80.

End effector 18 (FIGS. 1 and 13–16) includes the fixed jaw portion 96 and the movable jaw portion 98. Movable jaw portion 98 is coupled to the aforementioned jaw linkage 68 (FIG. 14) via a jaw linkage pin 100, such that when jaw linkage 68 is moved distally (i.e., by pulling jaw closing actuator 22 toward handle 14), jaw portion 98 is rotated about a pivot pin 102 (FIG. 13) and closes onto fixed jaw portion 96. Conversely, when jaw linkage 68 is moved proximally (i.e., by the power of biasing spring 69 acting on jaw linkage coupler 66 and hence jaw linkage 68), movable jaw portion 98 will open away from fixed jaw portion 96. It will be appreciated that the force of biasing spring 69 will normally keep movable jaw portion 98 open relative to fixed jaw portion 98 (FIGS. 1, 13 and 14), unless and until jaw closing actuator 22 is activated so as to overcome the bias of spring 69.

Wire cutting linkage 72 (FIGS. 2, 3, 14 and 15) is coupled to cutting bar 104 (FIGS. 14 and 15) that includes a small opening 106 through which suture wire 58 may pass, as will hereinafter be discussed in further detail. Preferably cutting bar 104 is slidably received in a passageway 107 (FIGS. 14, 15, 16 and 17H) formed in fixed jaw portion 96. In one position (FIG. 14), cutting bar 104 is positioned in fixed jaw portion 96 such that the cutting bar's opening 106 is aligned with a channel 108 formed in fixed jaw portion 96, whereby suture wire may be passed from the distal end of wire guide 76, through channel 108 formed in fixed jaw portion 96 (where it undergoes an approximately 90 degree change of direction), through opening 106 in cutting bar 104, through a channel extension 108A formed in fixed jaw portion 96, and across to movable jaw portion 98, as will hereinafter be discussed in further detail. However, when wire cutting linkage 72 is moved proximally by pulling wire cutting actuator 24 toward handle 14, cutting bar 104 is also moved proximally (FIG. 15) so as to cut any suture wire extending from channel 108 (in fixed portion 96) into opening 106 (in cutting bar 104). In this respect it will be appreciated that it is desirable to form channel extension 108A with a length greater than channel 108 (see FIGS. 14 and 15) so as to prevent the suture wire from being cut in two places (i.e., at channel 108 and again at channel extension 108A) when cutting bar 104 is moved proximally by pulling on wire cutting actuator 24. At the same time, however, it should also be appreciated that the fixed jaw portion's channel 108 and channel extension 108A, and the cutting bar's opening 106, are all sized, relative to suture wire 58, so as to provide as much support as possible to the suture wire as it passes through, and out of, fixed jaw portion 96.

It will be appreciated that the force of biasing spring 69 will normally keep cutting bar 104 in its distal position (i.e., with the cutting bar's opening 106 aligned with the fixed jaw portion's channel 108), unless and until wire cutting actuator 24 is activated so as to overcome the bias of spring 69.

In view of the foregoing construction, it will be seen that: (1) release lever 87 (FIGS. 8–10) may be activated so as to move wire follower wheel 92 away from, and toward, wire drive wheel 56 so as to permit a full wire supply cartridge 30 (FIGS. 1 and 5–7) to be loaded into suturing instrument 10; (2) activating jaw closing actuator 22 will cause movable jaw portion 98 to close on fixed jaw portion 96; (3) activating wire advance button 20 will cause wire drive wheel 56 to advance suture wire 58 through housing 12 and shaft 16; (4) activating rotation button 26 and/or rotation button 28 will cause shaft 16 to rotate relative to housing 12; and (5) activating wire cutting actuator 24 will cause cutting bar 104 to move proximally so as to sever any suture wire extending from fixed jaw portion 96.

Operation

Suturing instrument 10 may be used to apply wire suture 58 to a subject so as to effect a desired suturing operation.

By way of example but not limitation, and looking now at FIGS. 17A–17J, suturing instrument 10 may be used to suture together two portions 110, 112 of a subject which is to be sutured. In a typical case, portions 110, 112 might comprise two sections of severed tissue which need to be reattached to one another, or two pieces of previously unattached tissue which need to be attached to one another. However, one or the other of the portions 110, 112 might also comprise artificial mesh or some other object being attached to tissue, etc. In addition, in a typical case, portions 110, 112 might be located relatively deep within a patient, and might be accessed during a so-called "minimally invasive", or a so-called "closed surgery", procedure; however, in other circumstances, portions 110, 112 might be accessed during a conventional, or so-called "open surgery", procedure. This later situation might include procedures done at the outer surface of the patient's body, i.e., where portions 110, 112 comprise surface subjects.

In any case, suturing instrument 10 is initially prepared for use by installing batteries 34 into handle 14, if batteries 34 are not already installed, and by installing wire supply cartridge 30 into the suturing instrument, if a cartridge 30 is not yet installed. As noted above, wire supply cartridge 30 is installed in suturing instrument 10 by (1) moving the drive barrel assembly's release lever 87 to its open position (FIG. 9), so as to move wire follower wheel 92 away from wire drive wheel 56 and thereby expose the barrel assembly's central passageway 93; (2) passing the distal end of the cartridge (i.e., the distal end of wire guide 76) through drive barrel assembly 80 and shaft 16 until the distal end of wire guide 76 is in communication with the channel 108 formed in fixed jaw portion 96 (FIG. 14), at which point the cartridge's wire guide support unit 74 will be positioned intermediate wire drive wheel 56 and wire follower wheel 92 (FIG. 2); and (3) moving the drive barrel assembly's release lever 87 back to its closed position (FIG. 8), so as to cause wire drive wheel 56 and wire follower wheel 92 to extend through the wire guide's openings 78 and engage suture wire 58.

At this point suturing instrument 10 will be ready for use, with its movable jaw portion 98 being opened away from its fixed jaw portion 96, and with its cutting bar 104 being in its forward (FIG. 14) position.

Figure 17A:
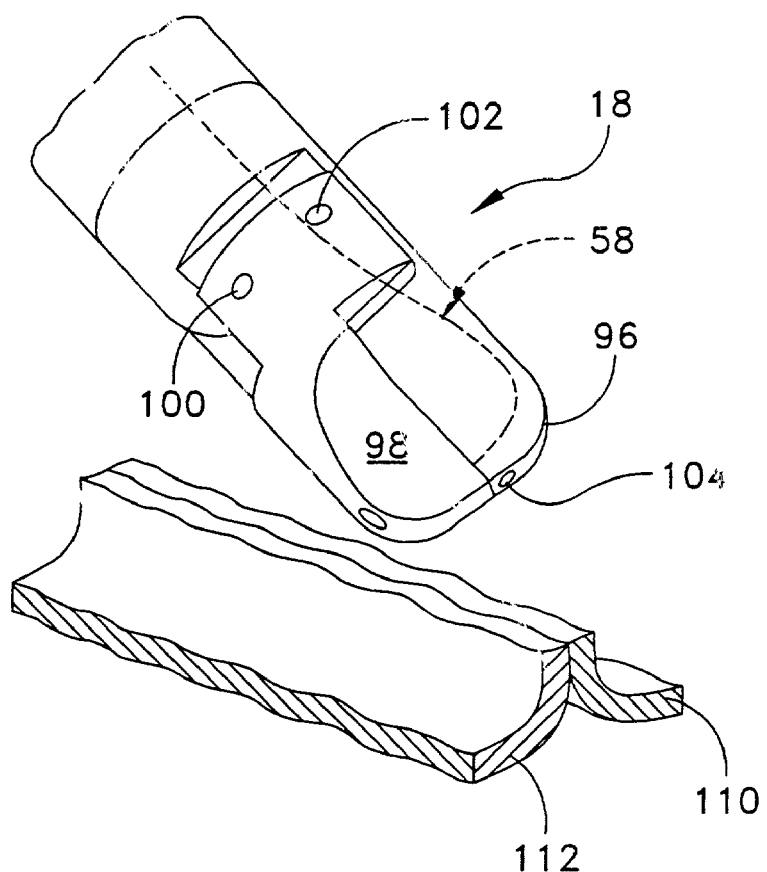
FIGS. 17A–17J show various steps in a suturing operation conducted with the suturing instrument shown in FIG. 1.

Next, suturing instrument 10 has its movable jaw portion 98 moved into engagement with its fixed jaw portion 96 (i.e., the jaws 96, 98 are placed in their "closed" position) by pulling jaw closing actuator 22 toward handle 14, and then the distal end of suturing instrument 10 is moved adjacent to subject portions 110, 112 (FIG. 17A).

In the case of a so-called closed surgical procedure, such positioning will generally involve moving the distal end of the suturing instrument through a cannula and into an interior body cavity; however, it is also envisioned that one might move the distal end of the suturing instrument directly into an otherwise-accessible body cavity, e.g., directly into the colon or esophagus, etc. In the case of a so-called open surgical procedure, such positioning might involve positioning the distal end of the suturing instrument adjacent to more readily accessible subject portions 110, 112.

Figure 17B:
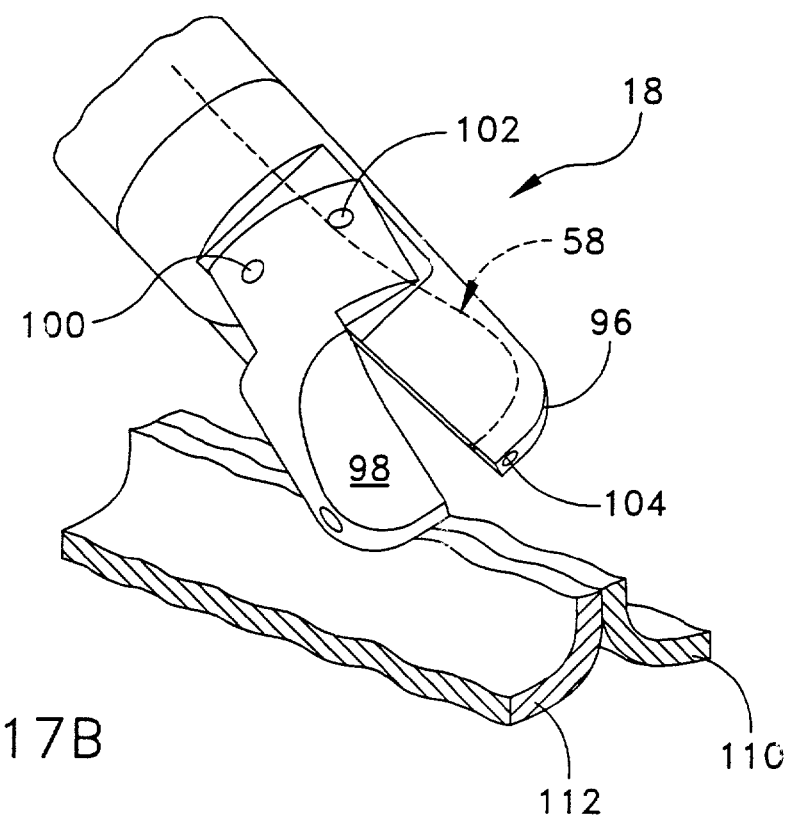
Figure 17C:
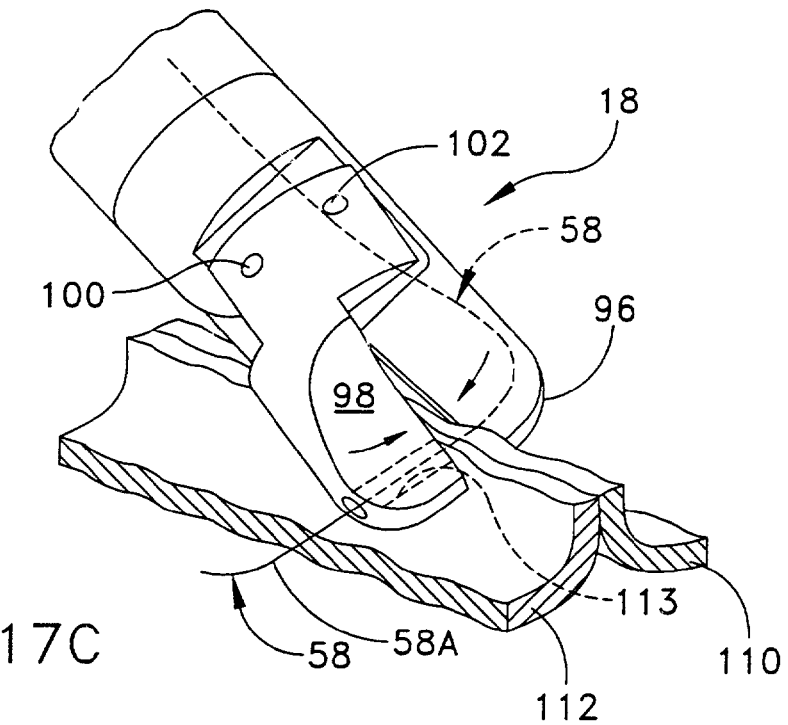

In any case, once the distal end of suturing instrument 10 has been placed adjacent to subject portions 110, 112, jaw closing actuator 22 is released, such that biasing spring 69 (FIG. 4) will cause movable jaw portion 98 to open away from fixed jaw portion 96 (FIG. 17B). Then the distal end of suturing instrument 10 is moved so that its jaws 96, 98 straddle subject portions 110, 112, and then jaw closing actuator 22 is actuated again, by pulling jaw closing actuator 22 toward handle 14, so as to close movable jaw portion 98 against fixed jaw portion 96, whereby to capture subject portions 110, 112 (FIG. 17C).

Next, wire advance button 20 is activated so as to cause suture wire 58 to be driven forward, out of the distal end of wire guide 76, through the fixed jaw portion's channel 108, through opening 106 in cutting bar 104, through the fixed jaw portion's channel extension 108A, through subject portions 110, 112, and finally through an opening 113 (FIGS. 14, 15 and 17C) formed in movable jaw portion 98. Suture wire 58 is preferably advanced so that a length 58A of wire 58 extends approximately 1 centimeter out of the bottom end of movable jaw portion 98 (FIG. 17C). In this respect it will be appreciated that, as suture wire 58 leaves fixed jaw portion 96 and engages subject portions 110, 112, the fixed jaw portion's channel 108, the cutting bar's opening 106 and the fixed jaw portion's channel extension 108A will support the thin suture wire so as to enable the suture wire to penetrate subject portions 110, 112.

Figure 17D:
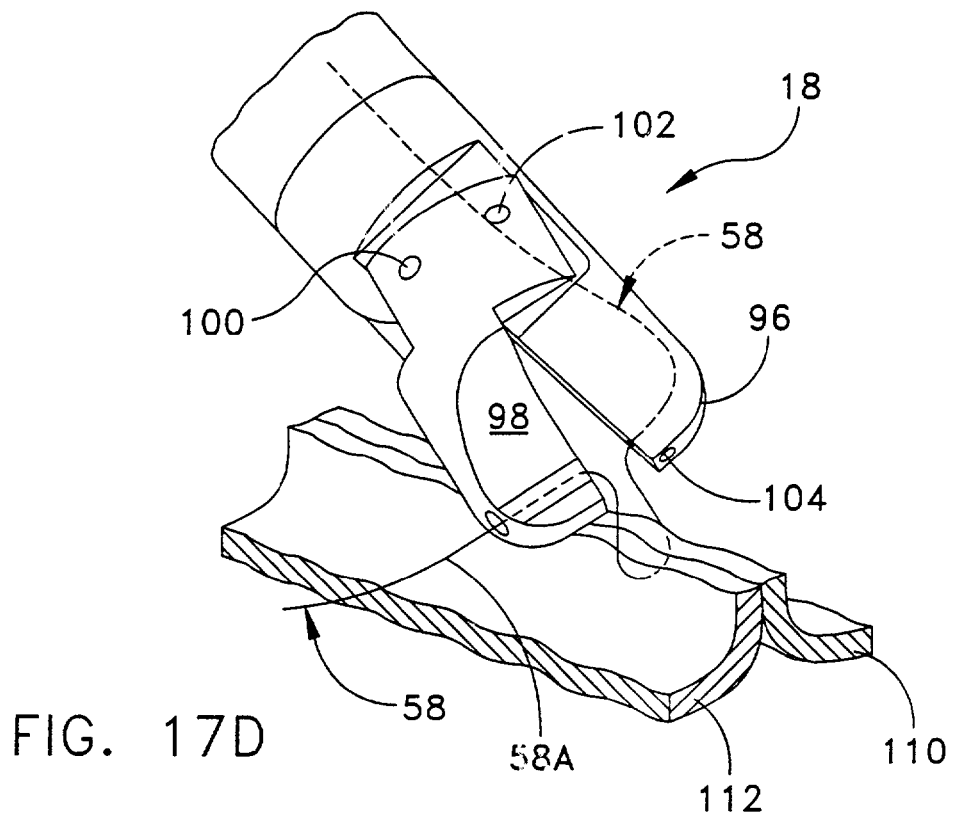

Once this has been done, jaw closing actuator 22 is released so as to permit movable jaw portion 98 to return to its "open" position relative to fixed jaw portion 96, and then wire advance button 20 is used to pay out additional suture wire 58 as the distal end of suturing instrument 10 is stepped back (e.g., by about a centimeter or so) from subject portions 110, 112 (FIG. 17D).

Figure 17E:
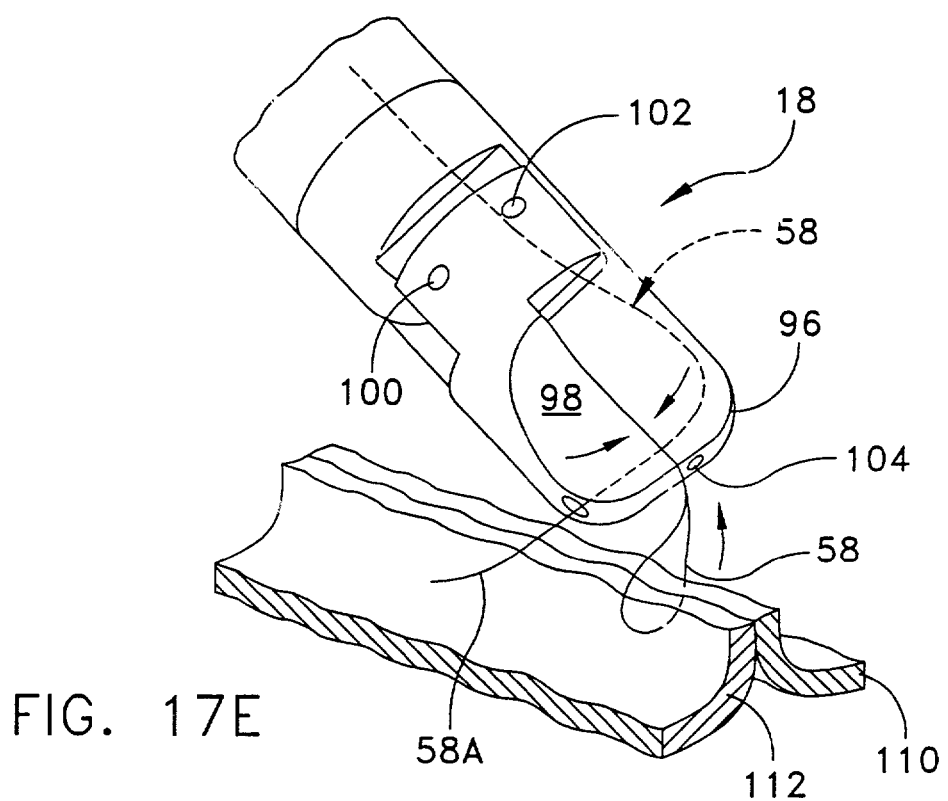
Figure 17F:
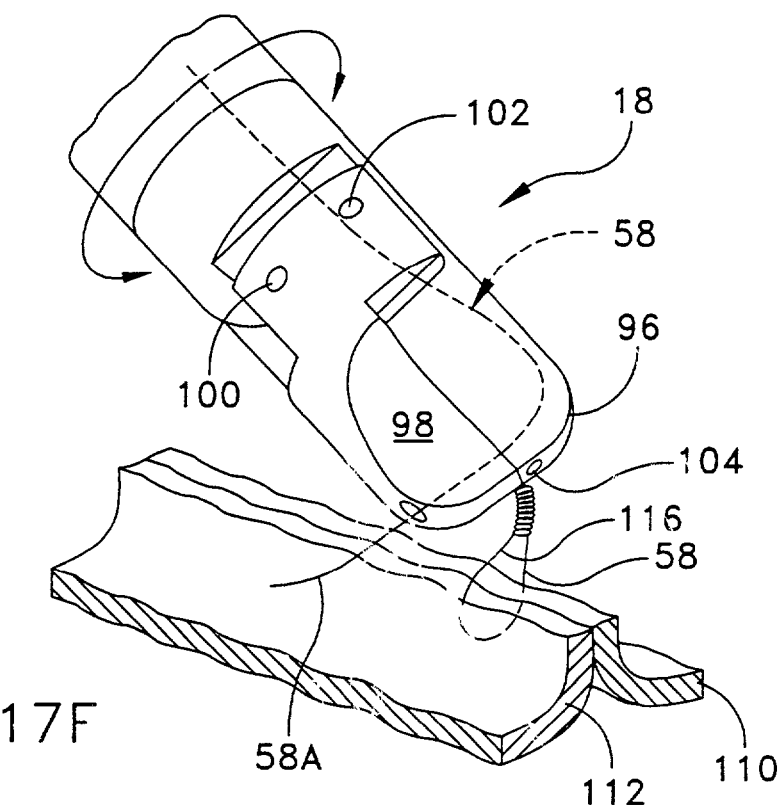
Figure 17G:
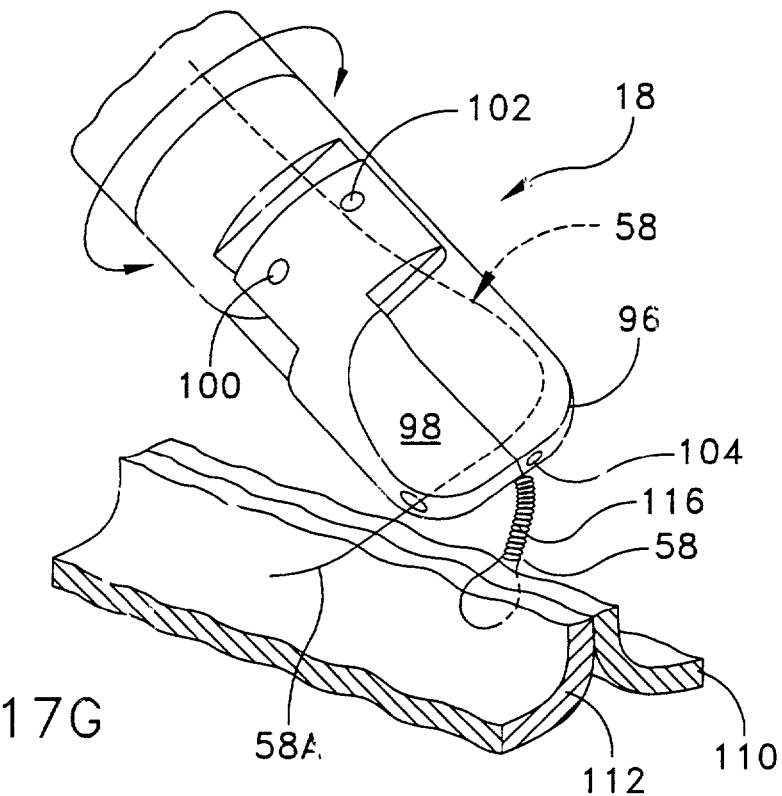
Figure 17H:
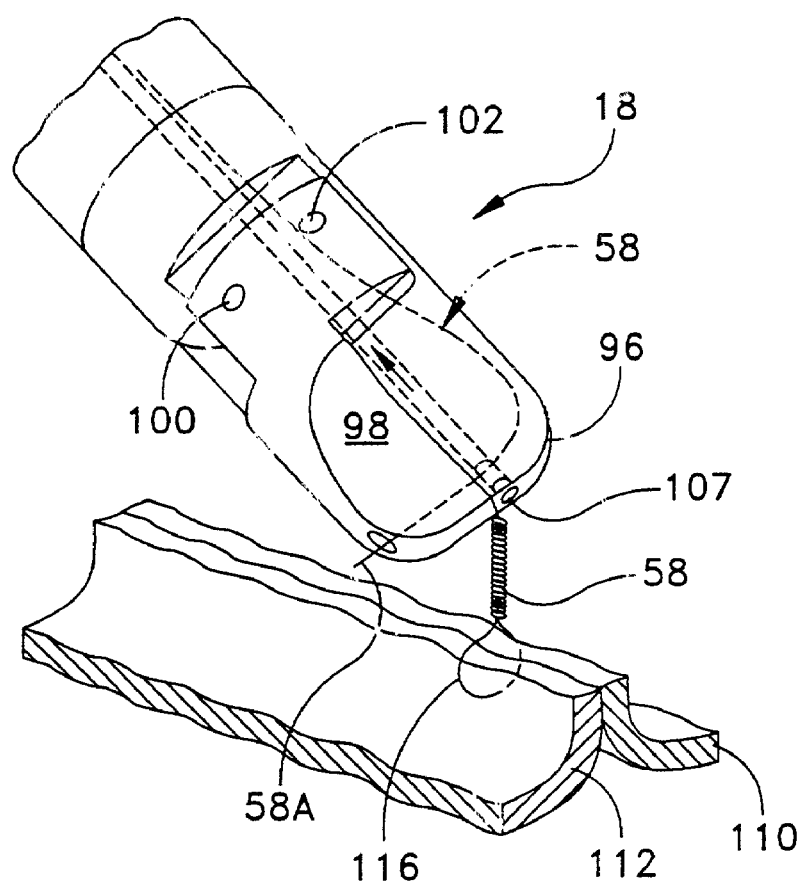

Then jaw closing actuator 22 is used to move jaw portion 98 back into engagement with fixed jaw portion 96 once more (FIG. 17E).

Next, left-thumb-actuated rotation button 26, or right-thumb-actuated rotation button 28, is used to rotate shaft 16 and hence end effector 18. This causes suture wire 58 to twist on itself, initially creating a relatively large loop 116 (FIG. 17F) of suture wire 58 extending from subject portions 110, 112 toward suturing instrument 10. However, as rotation button 26 and/or rotation button 28 is used to rotate shaft 16 (and hence end effector 18) more and more, the loop 116 of suture material will progressively close down (FIG. 17G) so as to form a tight binder for subject portions 110, 112. In this respect it will be appreciated that the longer the period of time that end effector 18 is rotated, the greater the amount of twisting of suture wire 58, and the greater the force holding subject portions 110, 112. In this respect it will also be appreciated that suture wire 58 is preferably carefully selected with respect to its flexibility relative to the strength of subject portions 110, 112. In particular, suture wire 58 is chosen so as to have a flexibility such that the suture wire will twist, and loop 116 will close down, before subject portions 110, 112 will undergo substantial deformation and/or tearing. By way of example but not limitation, in practice, it has been found that 0.005 inch diameter stainless steel wire can be used with most types of mammalian tissue such that the suture wire can be twisted closed without causing substantial deformation and/or tearing of the tissue.

Once suture wire 58 has been tightened to the desired degree, rotation of shaft 16 and end effector 18 is stopped, i.e., by releasing button 26 or button 28. Then wire cutting actuator 24 is depressed (e.g., it is pulled back toward handle 14) so as to pull cutting bar 104 proximally and thereby sever the suture wire 58 as the suture wire emerges from the fixed jaw portion's channel 108 and enters the cutting bar's opening 106. This action separates the deployed suture wire extending through subject portions 110, 112 from the suture wire remaining in wire supply cartridge 30, wire guide 76 and the fixed jaw portion's channel 108.

Figure 17I:
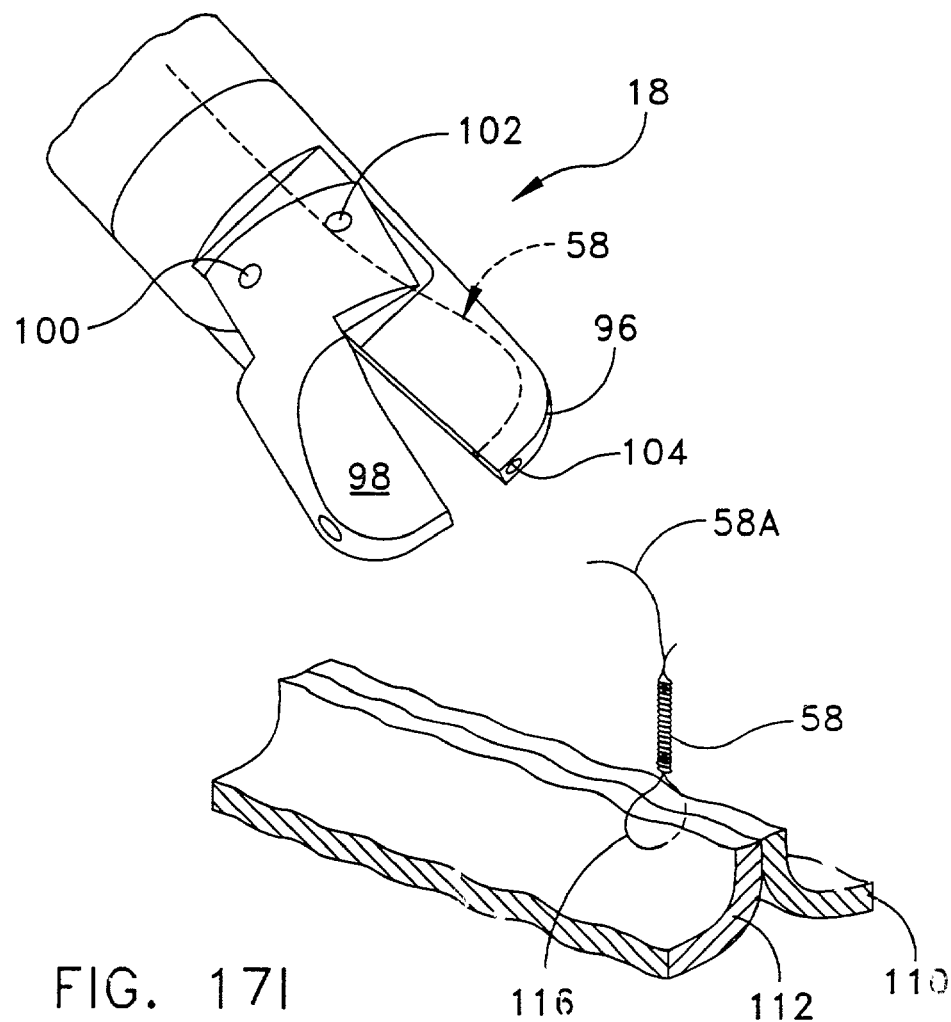

Then wire cutting actuator 24 is released, allowing biasing spring 69 to return cutting bar 104 to its distal position, and then jaw closing actuator 22 is released, allowing movable jaw portion 98 to move away from fixed jaw portion 96. Suturing instrument 10 may then be removed from subject portions 110, 112, which action will pull wire length 58A from movable jaw portion 98 (FIG. 17I).

Figure 17J:
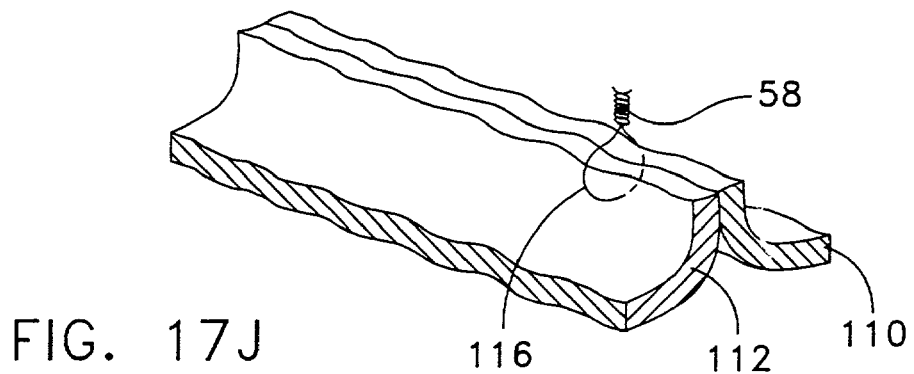

The deployed suture wire 58 may then be pressed down flat against subject portions 110, 112, or rounded into a ball, or otherwise operated upon, so as to reduce the profile of, or reduce the tendency to snag on, the deployed suture wire (FIG. 17J).

It will be appreciated that suturing instrument 10 will have application in a broad range of different suturing operations. More particularly, it will be appreciated that suturing instrument 10 will have application in both "open" and "closed" surgical procedures, with the former including, but not limited to, large entry procedures, relatively shallow procedures, and surface procedures; and with the latter including, but not limited to, surgical procedures where access is gained to an interior structure through the use of a cannula, and surgical procedures where access is gained directly to an internal body cavity without the use of a cannula, e.g., such as a procedure conducted within the colon or the esophagus.

It will also be appreciated that suturing instrument 10 will have application where two portions of tissue must be attached to one another (e.g., where two severed pieces of tissue must be re-attached to one another, or where two separate pieces of tissue must be attached to one another, or where two sections of a single piece of tissue must be approximated to one another), and where an object must be attached to the patient (e.g., where surgical mesh must be attached to the patient's abdominal wall during hernia repair surgery, etc.).

Among other things, it is believed that suturing instrument 10 will have particular application in the areas of general laparoscopic surgery, general thoracic surgery, cardiac surgery, general intestinal surgery, vascular surgery, skin surgery and plastic surgery.

Looking next at FIGS. 18 and 19, it will be seen that where the fixed jaw portion's channel 108 is disposed so as to be substantially aligned with the center of cutting bar 104 (FIG. 18), suture wire 58 will be cut with a relatively flat leading end 58B (FIG. 19). However, it has sometimes been found helpful to provide suture wire 58 with a relatively sharp leading point. Such a leading point can help open the subject for the following portion of the suture wire. In addition, such a leading point can help the suture wire penetrate the subject with a substantially straight path, so that the suture wire will reliably enter the movable jaw portion's opening 113. To this end, it has been found that moving the fixed jaw portion's channel 108 off-center relative to cutting bar 104 (FIG. 20) will cause the leading end 58B of suture wire 58 to be formed with a relatively sharp tip 58C (FIG. 21).

It is also possible to use suturing instrument 10 to ligate a subject rather than to pass a suture through the subject. For example, suturing instrument 10 might be used to ligate a blood vessel with suture wire 58. In this case, suturing instrument 10 is deployed so that suture wire 58 will pass around the far side of the subject, rather than through the subject as in the case of the suturing operation of the type described above.

By way of example but not limitation, in a typical ligating operation, movable jaw portion 98 is first opened relative to fixed jaw portion 96. Then suturing instrument 10 is positioned about the subject so that when movable jaw portion 98 is thereafter closed toward fixed jaw portion 96, the fixed jaw portion's channel 108 and the movable jaw portion's opening 113 will both lie on the far side of the subject. The movable jaw portion 98 is then closed against the fixed jaw portion 96, and suture wire 58 is passed from fixed jaw portion 96 to movable jaw portion 98, i.e., around the far side of the subject. The movable jaw portion 98 is then opened, and suture wire 58 is payed out as the instrument is stepped back from the subject. Then the movable jaw portion 98 is again closed against the fixed jaw portion 96. The shaft of the instrument is then rotated so as to form, and then close down, the ligating loop. Then cutting bar 104 is activated so as to cut the ligating loop from the remainder of the suture wire still in the tool, the movable jaw member 98 is opened, and the instrument is withdrawn from the surgical site. The deployed suture wire 58 may then be pressed down flat against the subject, or rounded into a ball, or otherwise operated upon, so as to reduce the profile of, or reduce the tendency to snag on, the deployed suture wire. As will be appreciated by a person skilled in the art, where instrument 10 is to be used for ligating purposes, fixed jaw portion 96 and movable jaw portion 98 might be formed with a greater longitudinal length so as to facilitate passing the suture wire around the far side of the subject. Furthermore, movable jaw member 98 might be formed with a recess, intermediate its jaw linkage pin 100 (FIG. 15) and its opening 113, for accommodating the subject, whereby to prevent compressing the subject when movable jaw member 98 is moved into engagement with fixed jaw member 96.

Suture wire 58 may comprise a wire formed out of a metal or any other suitable material having the required flexibility and stiffness. By way of example but not limitation, suture wire 58 may comprise stainless steel, titanium, tantalum, etc.

If desired, suture wire 58 may also be coated with various active agents. For example, suture wire 58 may be coated with an anti-inflammatory agent, or an anti-coagulant agent, or an antibiotic, or a radioactive agent, etc.

Figure 22:
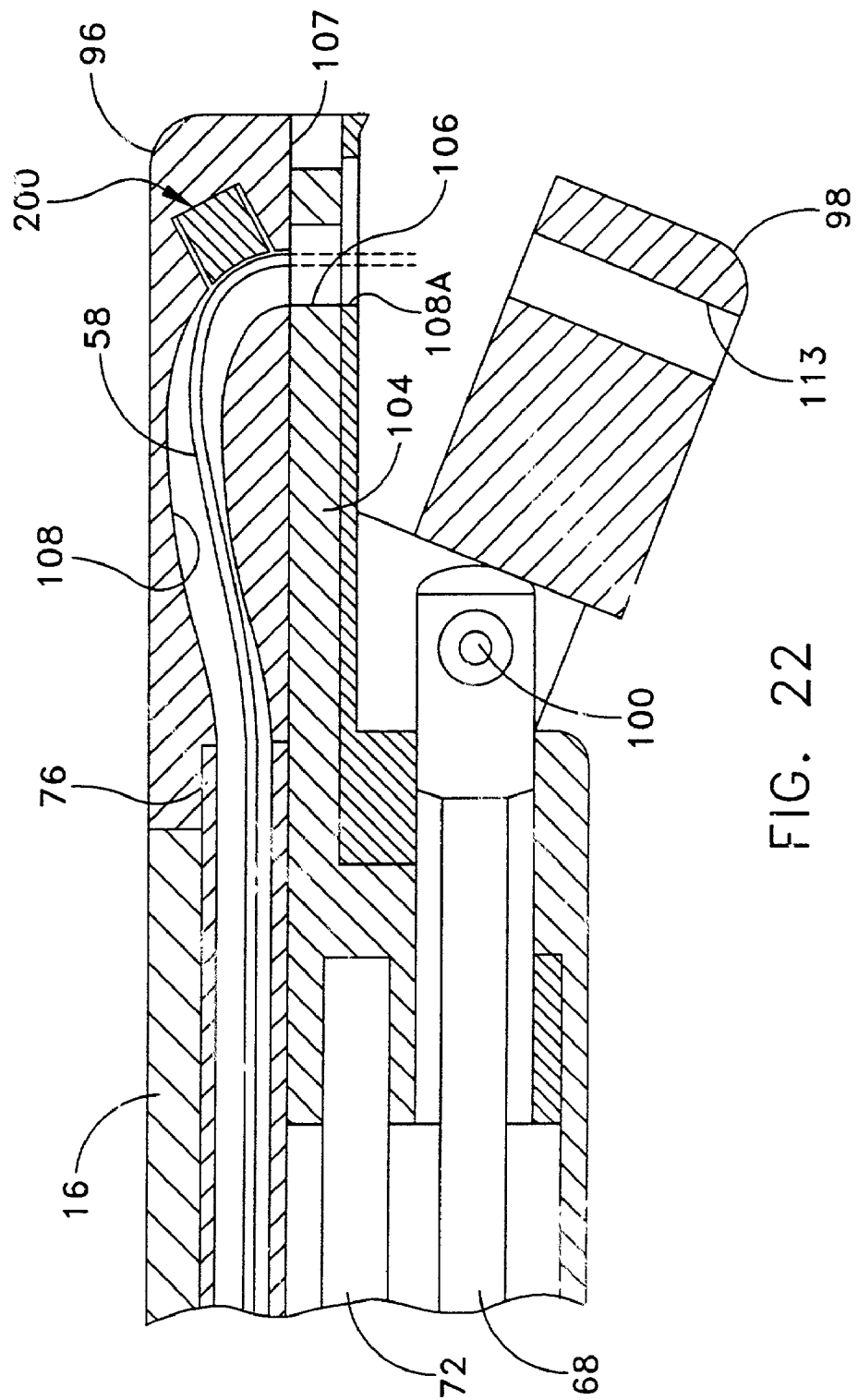
FIG. 22 is a side view, partially in section, of the end effector portion of the device, wherein the end effector portion includes a piezoelectric element to aid in wire penetration.

Looking next at FIG. 22, it is also possible to impart ultrasound energy to the wire in order to make tissue penetration easier. More particularly, because of the small cross-sectional area of the wire and the propensity for the wire to buckle when axially loaded, it is beneficial to be able to advance the wire into tissue with a minimum of load. This can be achieved by appropriately applying ultrasound energy to the wire.

A piezoelectric element 200 is placed at the outside radius of the wire guide path 108 at the right angle bend in the fixed jaw portion 96 just before where the wire enters the tissue. The piezoelectric element 200 vibrates at a position along this bend such that it supports the wire in completing the turn but also imparts a component of displacement in the direction of the tissue. Displacement of this kind at ultrasonic frequencies, in addition to the existing wire driving means, would cause the tip of the wire to penetrate the tissue using less force. In addition to reducing the tendency for outright wire buckling, lowering the wire loads will also allow the wire penetration to proceed in a straighter path.

Figure 23A:
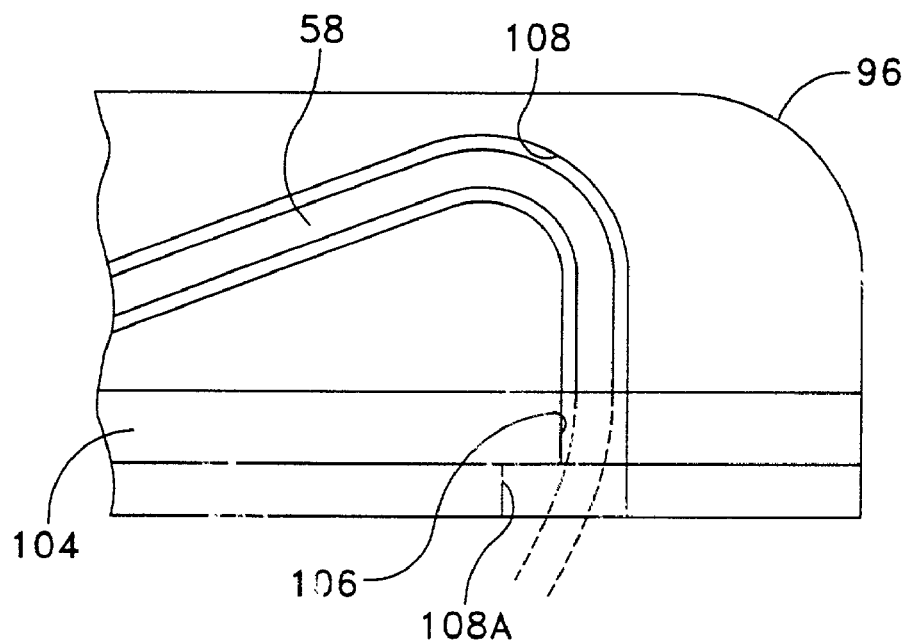
FIG. 23A is a schematic diagram of the device's fixed jaw portion, illustrating how the suture wire may sometimes curve as it exits the fixed jaw portion.
Figure 23B:
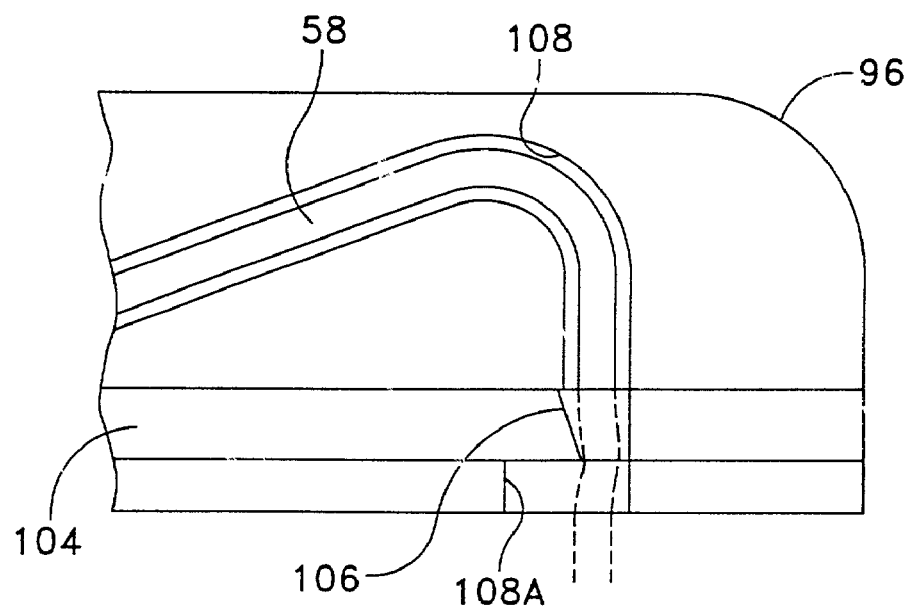
FIG. 23B is a schematic diagram of a modified form of the device's fixed jaw portion, illustrating how the profile of the device can be modified so as to counteract the aforementioned wire curvature.
Figure 23C:
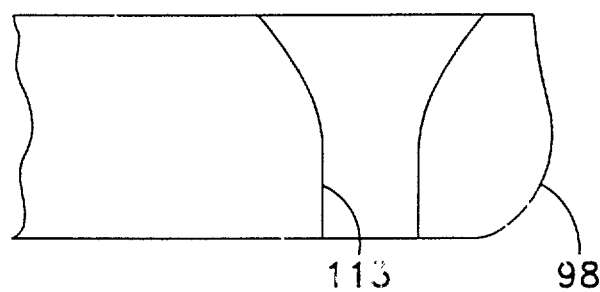
FIG. 23C is a schematic diagram of a modified form of the device's movable jaw portion, illustrating how the mouth of the movable jaw portion's opening may be enlarged so as to facilitate suture capture.

Looking next at FIG. 23A, it will be seen that, in some circumstances, the suture wire 58 may exit fixed jaw portion 96 with a curvature, due to the fact that suture wire 58 follows a curved channel 108 in fixed jaw portion 96. In some cases this curvature in the suture wire 58 may be quite modest, so that it may be effectively ignored. However, in other circumstances, this curvature might be large enough to cause the suture wire advancing out of fixed jaw portion 96 to miss the target opening 113 in movable jaw portion 98. In this case the curvature in suture wire 58 can present a significant problem. However, and looking now at FIG. 23B, it has been found that the profile of the cutting bar's opening 106 may be modified so as to provide a deflecting die which will counteract undesirable curvature in the suture wire and return the suture wire to a straight path as the suture wire exits fixed jaw portion 96. Alternatively, the profile of the fixed jaw portion's channel 108 may be modified, adjacent to cutting bar 104, so as to provide a similar deflecting die which will counteract undesirable curvature in the suture wire and return the suture wire to a straight path as the suture wire exits fixed jaw portion 96. Furthermore, and looking now at FIG. 23C, the mouth of the movable jaw portion's opening 113 may be enlarged to help capture a suture wire deviating from a straight path.

Figure 24:
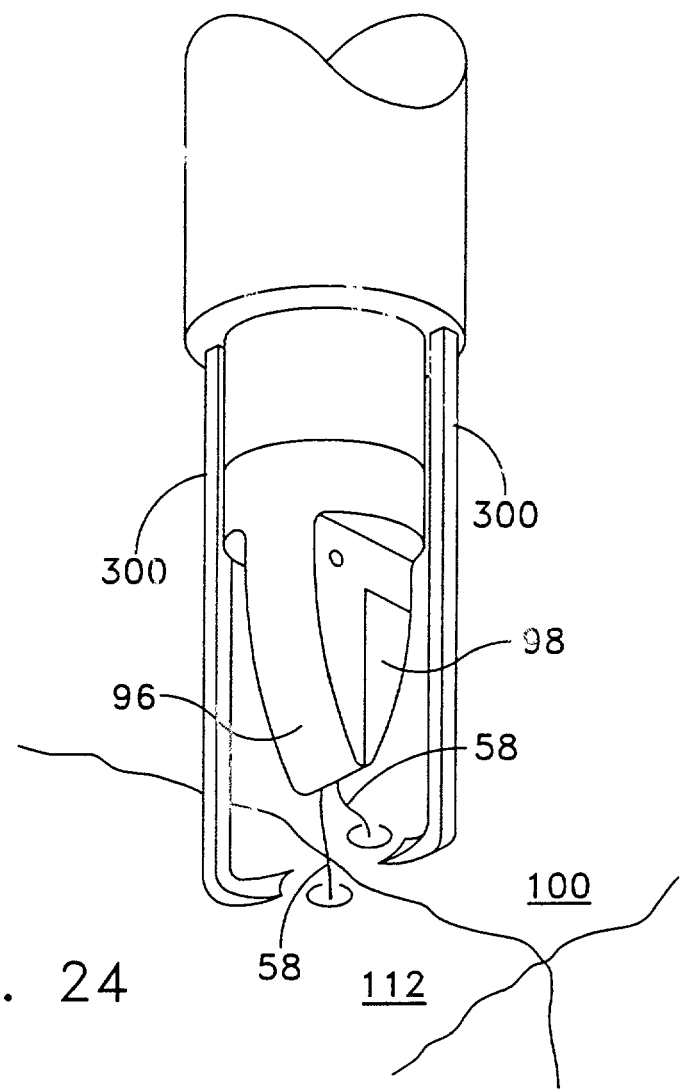
FIG. 24 is a schematic diagram of a modified form of the device, wherein one or more legs have been provided to help stabilize the tissue during suturing.

Looking next at FIG. 24, it will be seen that one or more legs 300 may be provided on suturing instrument 10, wherein legs 300 help stabilize the tissue during suturing.

Figure 25:
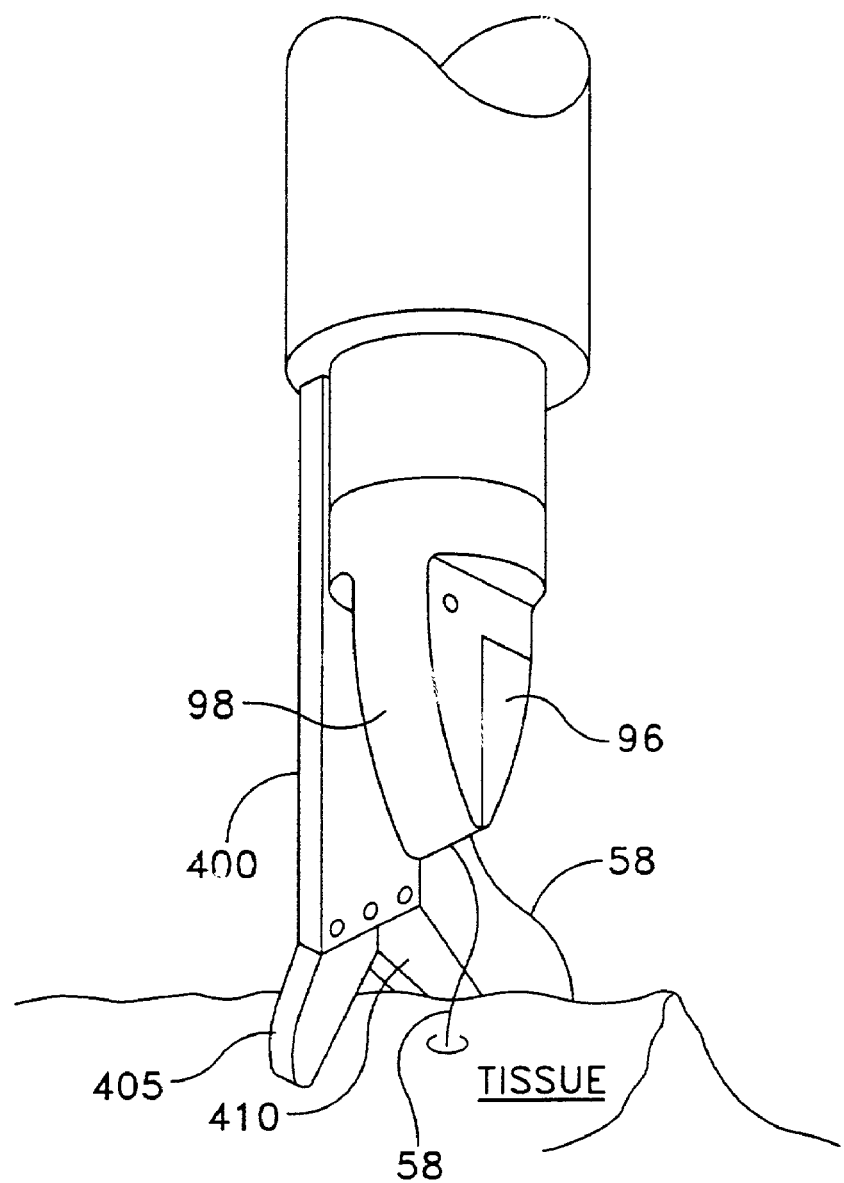
FIG. 25 is a schematic diagram of another modified form of the device, wherein a second set of jaws have been added to the device to help stabilize the tissue during suturing.

And looking next at FIG. 25, it will be seen that a grasper 400, comprising jaws 405 and 410, may be added to suturing instrument 10 to help stabilize the tissue during suturing.

If desired, the end effector 18 of suturing instrument 10 may be constructed so as to have two movable, opposing jaws, rather than one fixed jaw and one movable jaw as described above.

Also, if desired, shaft rotation motor 60 and thumb buttons 26, 28 may be configured so that depressing one button (e.g., button 26) will cause end effector 18 to rotate in one direction (e.g., clockwise), and depressing the other button (e.g., button 28) will cause end effector 18 to rotate in the opposite direction (e.g., counterclockwise).

Figure 26:
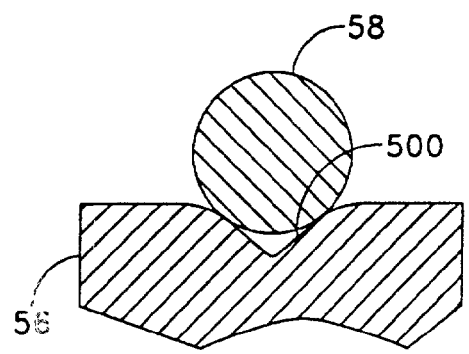
FIG. 26 is a sectional view of part of a drive wheel portion of the drive barrel assembly of FIG. 9, showing an alternative embodiment of drive wheel.

Referring to FIG. 26, it will be seen that the drive wheel 56 may be provided with a peripheral v-shaped groove 500 for receiving the suture wire 58. The groove 500 provides greater contact area in the wire gripping surface of the wheel, decreasing the possibility of slippage between the wheel 56 and the suture 58.

Similarly, an arc-shaped groove 502 (FIG. 27) may be provided. It is preferable that the arc of the groove 502 be a portion of a hypothetical circle having a diameter slightly greater than the diameter of the suture wire 58.

Figure 28:
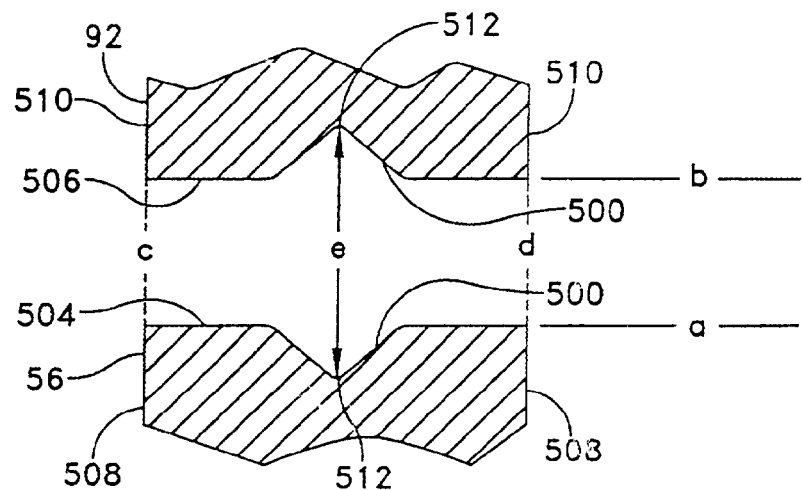
FIG. 28 is a sectional view similar to FIG. 26, but showing part of opposed wheels of the type shown in FIG. 26.

As is shown in FIG. 28, both the drive wheel 56 and the wire follower wheel 92 may be provided with a groove 500. When both wheels 56, 92 are provided with grooves, it is necessary that the wheel driving edges 504, 506 define planes, a and b, which are precisely parallel. It further is necessary that side surfaces 508, 510 of the wheels 56, 92 reside in planes c, d precisely parallel to each other, and that centers 512 of the grooves 500 be aligned in a plane e parallel to planes c and d and normal to planes a and b. Misalignment of the wheels 56, 92 can cause twisting and bunching of the suture 58 and failure in advancing the suture properly and/or mis-direction of the wire upon emergence from the instrument.

The drive wheel alone, or both the drive wheel 56 and the follower wheel 92, may be provided with multiple grooves (not shown) of different sizes to accommodate suture wires of different sizes, such that various sizes of wire may be used in a single instrument.

It should also be appreciated that, if desired, wheels 56 and 92 may both be driven, rather than just drive wheel 56.

Figure 29:
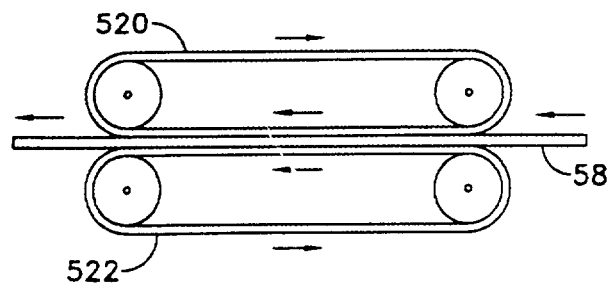
FIG. 29 is a diagrammatic illustration of an alternative suture wire drive assembly for the drive barrel assembly of FIG. 9.
Figure 42:
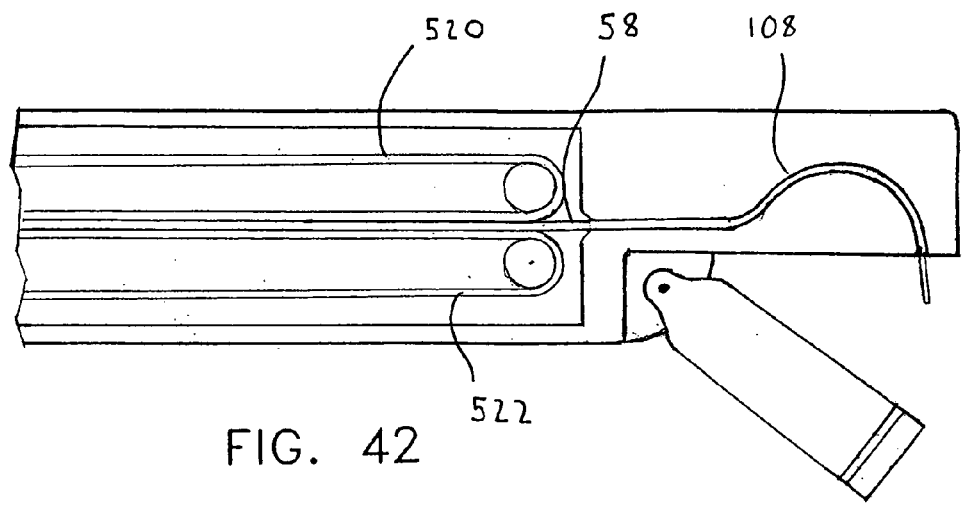
FIG. 42 is a cross sectional view showing the wire drive of FIG. 29 located adjacent a distal end of an elongated shaft of the instrument.

Referring to FIG. 29, it will be seen that instead of wheels 56, 92 engaging the suture wire 58, there may be provided opposed roller-driven treads, or conveyor belts 520, 522. While the belts 520, 522 may be used in place of the wheels 56, 92 in the drive barrel assembly 80, they may alternatively be placed further forward, or distally in the instrument, as shown in FIG. 42, so as to effect pulling of the wire 58 through the instrument, rather than pushing the wire, thereby eliminating the aforementioned problems of bending and buckling, associated with pushing a flexible strand.

Figure 27:
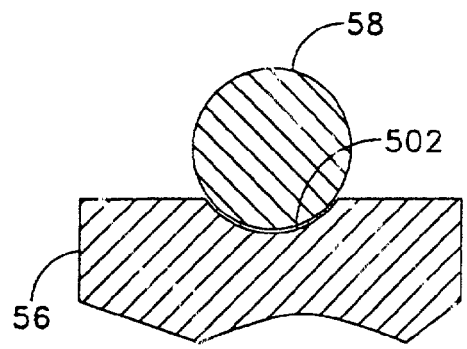
FIG. 27 is similar to FIG. 26, showing an alternative embodiment of drive wheel.

The conveyor belts 520, 522 may be provided with grooves of the type shown in FIGS. 26 and 27, or may be provided with flat wire-engaging surfaces.

Figure 30:
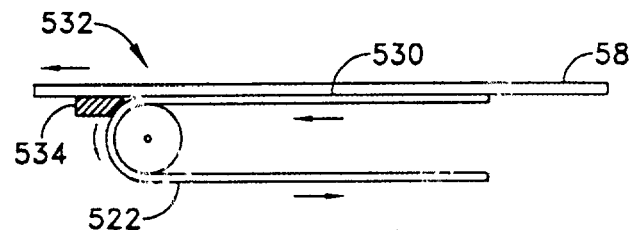
FIG. 30 is a diagrammatic illustration of another alternative embodiment of suture wire drive assembly.
Figure 31:
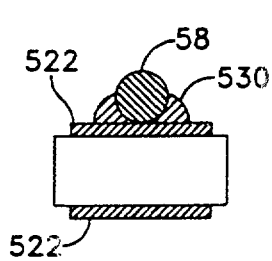
FIG. 31 is a width-wise generally sectional view of the drive assembly of FIG. 30.
Figure 32:
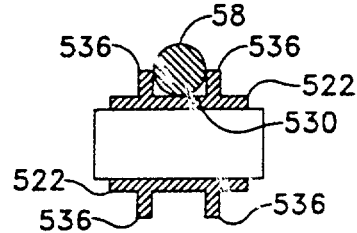
FIGS. 31a and 32 are similar to FIG. 31, but illustrative of further alternative embodiments.
Figure 31A:
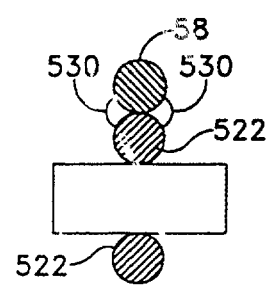

In FIGS. 30 and 31, there is shown a further alternative embodiment of wire drive assembly wherein the suture wire 58 is attached to the belt 522, as by adhesive 530. At the delivery end 532 of the assembly, there is provided a blade 534 for stripping the suture wire 58 from the belt 522. As is shown in FIG. 32, the belt 522 may be provided with lengthwise extending ribs 536 between which rides the wire 58. The ribs 536 provide insurance against the possibility of the wire moving off-center on the belt 522. Alternatively, as shown in FIG. 31a, the belt 522 may comprise a carrier wire, or thread, to which the suture wire is bound and from which the suture wire is separable by the blade 534.

Figure 33:
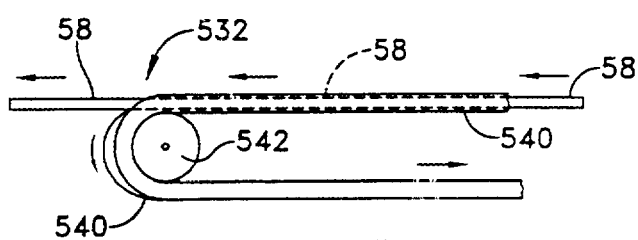
FIG. 33 is a diagrammatic illustration of still another alternative embodiment of suture wire drive assembly.
Figure 34:
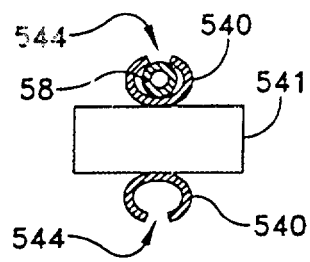
FIG. 34 is a width-wise generally sectional view of the drive assembly of FIG. 33.
Figure 35:
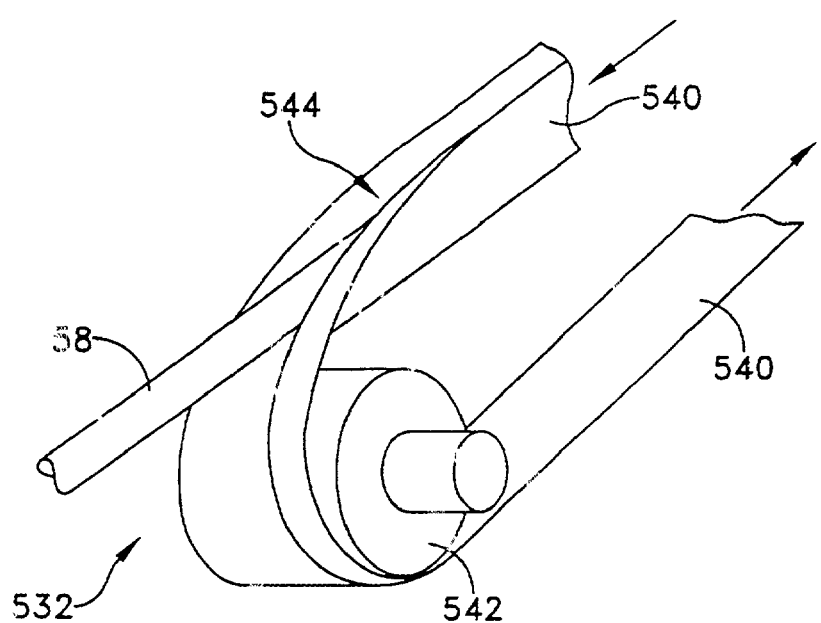
FIG. 35 is a perspective view of the drive assembly of FIGS. 33 and 34.
Figure 43:
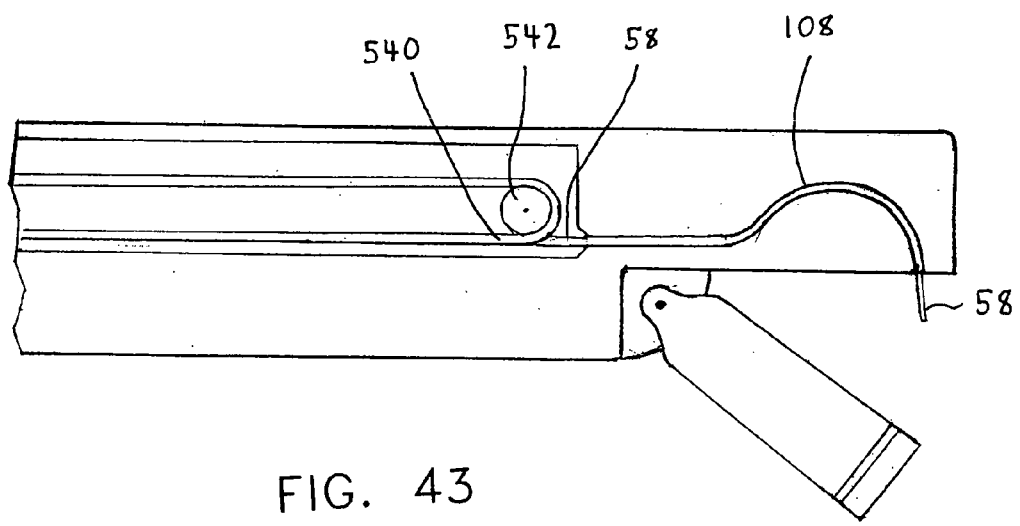
FIG. 43 is a cross sectional view showing the wire drive of FIG. 34 located adjacent a distal end of an elongated shaft of the instrument.
Figure 44:
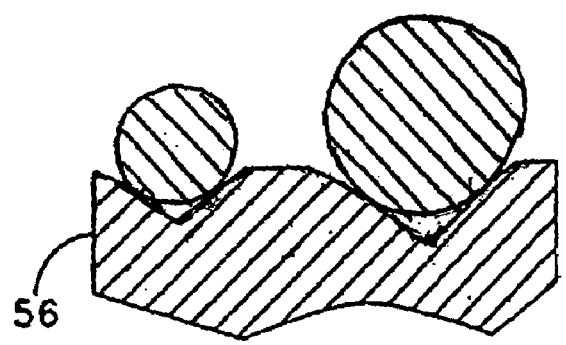
FIG. 44 is a sectional view of part of a drive wheel portion of a drive barrel assembly showing an embodiment having multiple grooves to engage suture wires of different sizes.

In FIGS. 33–35, it will be seen that instead of the belt or carrier wire or thread 522, there may be provided a tube 540 driven by rollers 542 (one shown in FIGS. 33–35). The tube 540 is provided with a lengthwise endless slit 544 and is of a size to house the suture wire 58. At the delivery end 532 of the assembly, the wire 58 is guided, as by the blade 534, shown in FIG. 30, out of the tube 540, by way of the slit 544. As in the previously described embodiments featuring conveyor belts, or the like, the drive assembly shown in FIGS. 33–35 preferably is placed near the distal end of the instrument, as shown in FIG. 43, such that the wire 58 may be in large measure pulled, rather than pushed.

Figure 36:
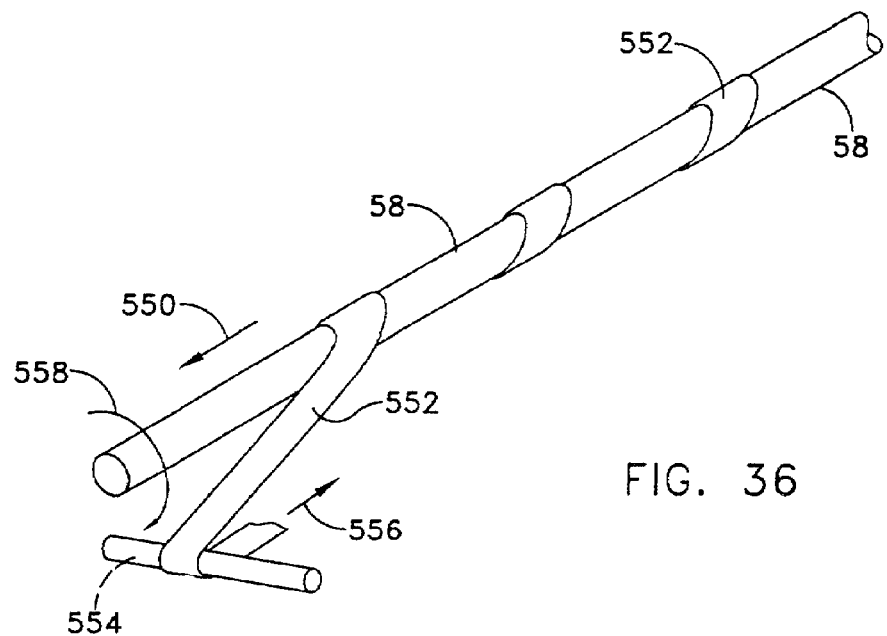
FIG. 36 is a diagrammatic perspective view of still another alternative embodiment of suture wire drive assembly.

Referring to FIG. 36, it will be seen that in another alternative drive assembly, the suture wire 58 is pulled in the direction of arrow 550 by a strap 552 passed around a roller 554 and returned by a drive wheel, or the like (not shown) in the direction of arrow 556. In this embodiment, in addition to linear motion of the wire 58 in the direction of arrow 550, the wire is rotatively moved, as indicated by arrow 558, to enhance tissue penetration.

Figure 37:
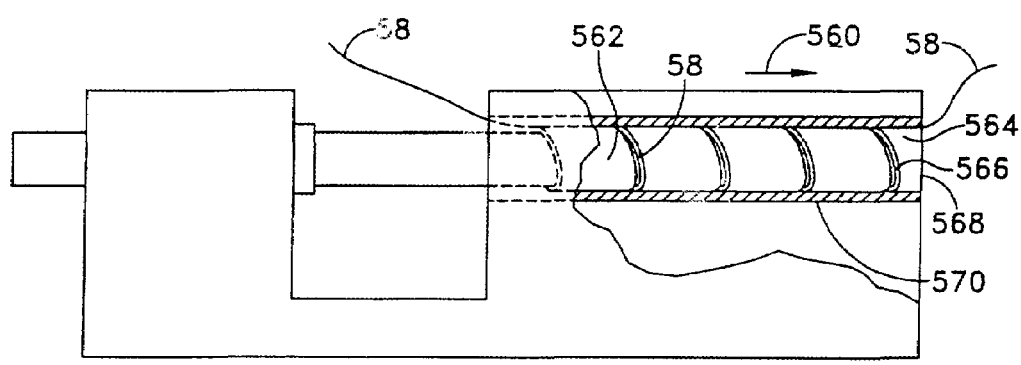
FIG. 37 is a diagrammatic side elevational view, broken away, illustrating another alternative embodiment of suture wire drive assembly.
Figure 38:
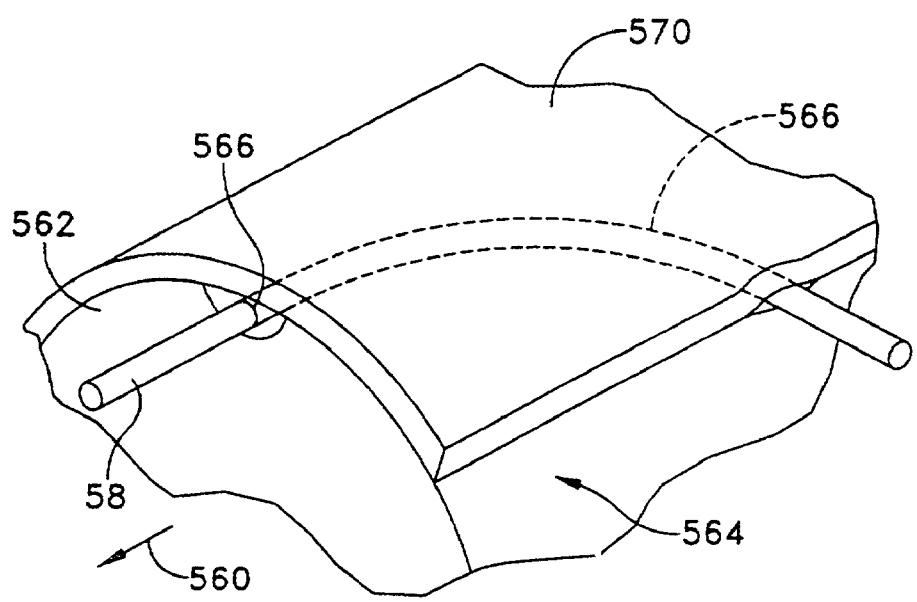
FIG. 38 is a perspective view of a portion of FIG. 37.

Referring to FIGS. 37 and 38, it will be seen that the suture wire 58 may be carried in the direction of arrow 560 by an auger 562 comprising a rotatable rod 564 having a spiral groove 566 therein. The wire 58 is disposed in the groove 566 and is carried therein toward a distal end 568 of the auger 562. A stationary rigid sleeve 570 is disposed around the auger 562 and covers the groove 566 such that the wire 58 radially is confined to the groove 566.

Figure 39:
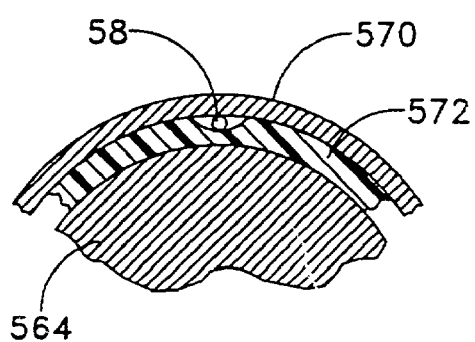
FIG. 39 is a cross sectional view showing an arrangement similar to that shown in FIG. 38, but modified.

In FIG. 39, there is shown an embodiment in which the rod 564 is not provided with a spiral groove, but rather is covered with an elastomeric tube 572. The stationary rigid sleeve 570 is disposed around the elastomeric tube 572. The wire 58 is wound around the elastomeric tube 572 and is held in place by the sleeve 570, which preferably is of a slippery polymer material. As the rod 564 is rotated, so is the elastomeric tube 572 which is fixed thereon. The tube 572 carries the wire 58 which is confined by the sleeve 570.

Figure 40:
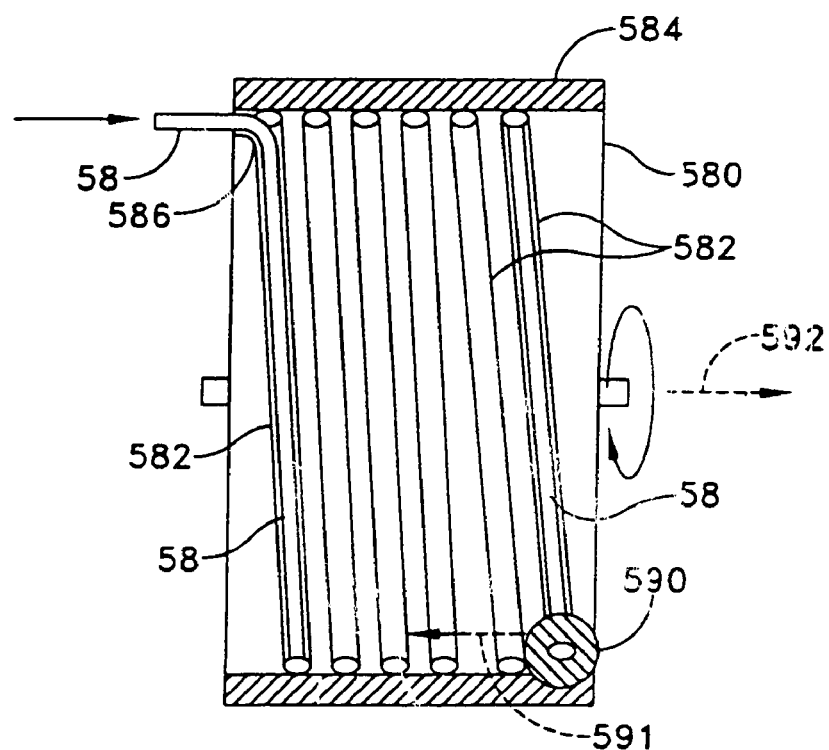
FIG. 40 is a diagrammatic front elevational view, partly in section, of still another alternative embodiment of suture wire drive assembly.
Figure 41:
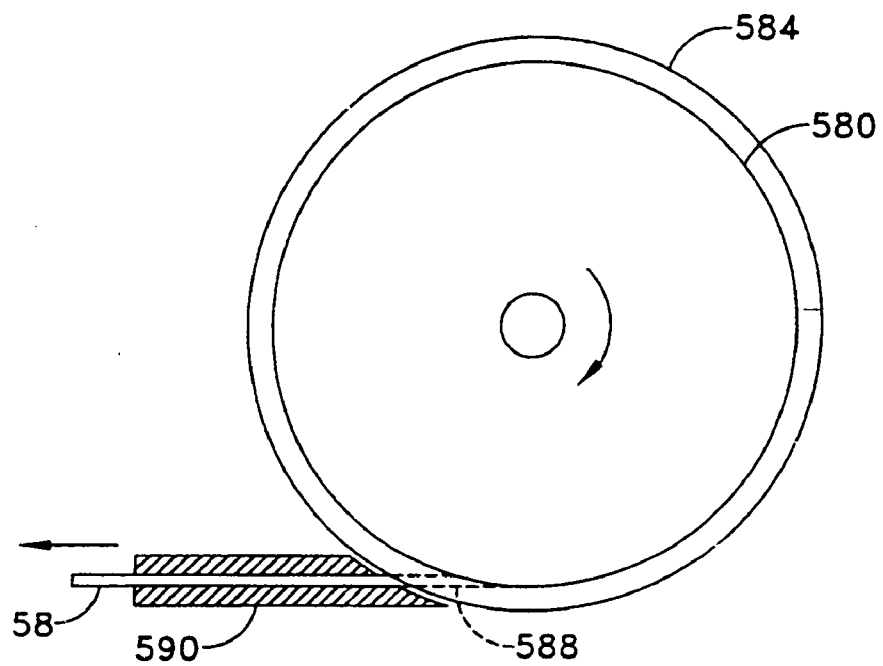
FIG. 41 is a side elevational view, partly in section, of the assembly of FIG. 40.

In FIGS. 40 and 41, there is shown still another suture wire drive assembly. In the assembly illustrated in FIGS. 40 and 41, there is provided a rotatable driver 580 having a spiral groove 582 therein and a rigid stationary sleeve 584 thereon. The groove 582 is provided with an inlet 586 for receiving the suture wire 58 and an outlet 588 for discharging the wire 58. Adjacent the outlet 588 is a guide tube 590 for directing and supporting the wire 58. In operation, rotation of the driver 580 causes spiral groove 582 to act as a sort of auger, carrying the wire 58 from the wire inlet 586 to the wire outlet 588. The driver 580 may be positioned at or near the distal end of the instrument, permitting pulling of the suture wire 58, rather than pushing the wire, with all its attendant problems mentioned herein above.

Alternatively, if desired, a predetermined quantity of wire 58 may be wound in the rotatable driver's spiral groove 582, and the inlet 586 omitted. In this case, driver 580 can just pay out wire, with guide tube 590 moving laterally, in the manner shown by the arrow 591 in FIG. 40, as driver 580 is rotated. Alternatively, if desired, guide tube 590 can remain stationary and driver 580 moved laterally, in the manner shown by the arrow 592 in FIG. 40.

MODIFICATIONS

It will be appreciated by those skilled in the art that numerous modifications and variations may be made to the above-disclosed embodiments without departing from the spirit and scope of the present invention.

What is claimed is:

1. A surgical device for passing a flexible elongated element through tissue of a subject, the device comprising:
 a flexible elongated element;
 an elongate shaft with a proximal end, a distal end with an opening, and a passageway adapted to deliver the elongated element toward the distal end and out of the opening;
 an advancement mechanism located adjacent the distal end of the elongated shaft and adapted to move the flexible elongated element in the passageway, the advancement mechanism having a first surface to engage a first lateral portion of the flexible elongated element such that movement of the first surface moves the flexible elongated element out of the opening with force sufficient to puncture the tissue;
 a compartment to store a length of the flexible elongated element in a coil in the surgical device; and
 a cutter adapted to cut the flexible elongated element near the distal end of the elongate shaft.

2. The surgical device of claim 1, wherein the surgical device is suitable for use in a closed surgical operation.

3. The surgical device of claim 2, further comprising:
 a second surface opposed to the first surface, the second surface adapted to engage a second lateral portion of the flexible elongated element such that movement of at least one of the first and second surfaces moves the flexible elongated element toward the distal end with force sufficient to penetrate the tissue.

4. The surgical device of claim 3, wherein the first surface has a first groove oriented to receive the first lateral portion of the flexible elongated element.

5. The surgical device of claim 4, wherein the second surface has a second groove oriented to receive the second lateral portion of the flexible elongated element.

6. The surgical device of claim 1, wherein the first surface has a first groove oriented to receive the first lateral portion of the flexible elongated element.

7. The surgical device of claim 1, further comprising:
 a guide tube disposed within the elongate shaft, the guide tube forming at least a portion of the passageway and constructed and arranged to closely support the flexible elongated element when moving toward the distal end.

8. The surgical device of claim 1, further comprising:
 a pair of operable jaws disposed at the distal end of the elongate shaft.

9. The surgical device of claim 1, wherein the passageway includes a curved portion adapted to impart curvature to the flexible elongated element passing through the passageway.

10. The surgical device of claim 1, wherein the flexible elongated element is used to form suture secured to tissue.

11. The surgical device of claim 1, wherein the first surface comprises a first belt surface of a first belt.

12. The surgical device of claim 11, wherein the first surface comprises an adhesive to engage the first lateral portion of the flexible elongated element.

13. The surgical device of claim 12, further comprising:
 a separator adapted to separate the flexible elongated element from the first surface.

14. The surgical device of claim 11, further comprising:
 a second belt surface of a second belt, the second belt surface opposed to the first belt surface and oriented along a second lateral portion of the flexible elongated element and adapted to engage the second lateral portion such that movement of the first and second belt surfaces moves the flexible elongated element in the passageway with force sufficient to penetrate the tissue.

15. The surgical device of claim 14, wherein at least one of the first or second belt surfaces includes a groove adapted to engage either the first or second lateral portions of the flexible elongated element.

16. The surgical device of claim 11, wherein the first belt comprises a tube with a lengthwise endless slit.

17. The surgical device of claim 16, further comprising:
 a separator adapted to separate the flexible elongated element from the tube through the slit.

18. The surgical device of claim 1, wherein the advancement mechanism comprises a sleeve and a substantially cylindrical rod with an outer surface having a spiral groove, the rod adapted rotate within the sleeve to move the flexible elongated element in the passageway.

19. A surgical device for passing a flexible elongated element through tissue of a subject, the device comprising:
   an elongate shaft with a proximal end, a distal end, and a passageway adapted to deliver the elongated element toward the distal end;
   an advancement mechanism located adjacent the distal end of the elongated shaft and adapted to move the flexible elongated element in the passageway, the advancement mechanism having a first surface adapted to engage a first lateral portion of the flexible elongated element such that movement of the first surface moves the flexible elongated element in the passageway; and
   a cutter adapted to cut the flexible elongated element.

20. The surgical device of claim 19, wherein the surgical device is suitable for use in a closed surgical operation.

21. The surgical device of claim 20, further comprising:
   a second surface opposed to the first surface, the second surface adapted to engage a second lateral portion of the flexible elongated element such that movement of at least one of the first and second surfaces moves the flexible elongated element toward the distal end.

22. The surgical device of claim 21, wherein the first surface has a first groove oriented to receive the first lateral portion of the flexible elongated element.

23. The surgical device of claim 22, wherein the second surface has a second groove oriented to receive the second lateral portion of the flexible elongated element.

24. The surgical device of claim 19, wherein the first surface has a first groove oriented to receive the first lateral portion of the flexible elongated element.

25. The surgical device of claim 24, wherein the first surface has a second groove of a size different than the first groove.

26. The surgical device of claim 19, wherein the flexible elongated element is used to form suture secured to tissue.

27. The surgical device of claim 19, further comprising:
   a guide tube disposed within the elongate shaft, the guide tube forming at least a portion of the passageway and constructed and arranged to closely support the flexible elongated element when moving toward the distal end.

28. The surgical device of claim 19, further comprising:
   a compartment to store a length of the flexible elongated element provided to the advancement mechanism.

29. The surgical device of claim 28, wherein the compartment is adapted to store the length in a coil.

30. The surgical device of claim 19, further comprising:
   a pair of operable jaws disposed at the distal end of the elongate shaft.

31. The surgical device of claim 19, wherein the passageway includes a curved portion adapted to impart curvature to the flexible elongated element passing through the passageway.

32. The surgical device of claim 19, wherein the first surface comprises a first belt surface of a first belt.

33. The surgical device of claim 32, further comprising:
   a second belt surface of a second belt, the second belt surface opposed to the first belt surface and oriented along a second lateral portion of the flexible elongated element and adapted to engage the second lateral portion such that movement of the first and second belt surfaces moves the flexible elongated element in the passageway with force sufficient to penetrate the tissue.

34. The surgical device of claim 33, wherein at least one of the first or second belt surfaces includes a groove adapted to engage either the first or second lateral portions of the flexible elongated element.

35. The surgical device of claim 32, wherein the first surface comprises an adhesive to engage the first lateral portion of the flexible elongated element.

36. The surgical device of claim 35, further comprising:
   a separator adapted to separate the flexible elongated element from the first surface.

37. The surgical device of claim 32, wherein the first belt comprises a tube with a lengthwise endless slit.

38. The surgical device of claim 37, further comprising:
   a separator adapted to separate the flexible elongated element from the tube through the slit.

39. The surgical device of claim 19, wherein the advancement mechanism comprises a sleeve and a substantially cylindrical rod with an outer surface having a spiral groove, the rod adapted rotate within the sleeve to move the flexible elongated element in the passageway.

40. A surgical device for passing a flexible elongated element through tissue of a subject, the device comprising:
   a flexible elongated element;
   an elongate shaft with a proximal end, a distal end with an opening, and a passageway adapted to deliver the elongated element toward the distal end and out of the opening;
   an advancement mechanism located adjacent the distal end of the elongated shaft and adapted to move the flexible elongated element in the passageway, the advancement mechanism having a first surface to engage a first lateral portion of the flexible elongated element such that movement of the first surface moves the flexible elongated element out of the opening with force sufficient to puncture the tissue;
   a compartment to store a length of flexible elongated element in a coil in the surgical device; and
   a pair of operable jaws disposed at the distal end of the elongated shaft.

* * * * *